United States Patent
Riley et al.

(10) Patent No.: US 9,644,179 B2
(45) Date of Patent: May 9, 2017

(54) USE OF PDL1 EXPRESSING CELLS TO CONVERT T CELLS INTO REGULATORY T CELLS

(71) Applicants: THE TRUSTEES OF THE UNIVERSITY OF PENNSYLVANIA, Philadelphia, PA (US); The United States of America, as Represented by the Secretary of the Department of Health and Human Services, Washington, DC (US)

(72) Inventors: James L. Riley, Downingtown, PA (US); Daniel H. Fowler, Bethesda, MD (US); Shoba Amarnath, Washington, DC (US)

(73) Assignees: The Trustees of the University of Pennsylvania, Philadelphia, PA (US); The United States of America, as Represented By The Secretary, Department of Health And Human Services, Washington, DC (US)

( * ) Notice: Subject to any disclaimer, the term of this patent is extended or adjusted under 35 U.S.C. 154(b) by 173 days.

(21) Appl. No.: 14/359,764

(22) PCT Filed: Nov. 20, 2012

(86) PCT No.: PCT/US2012/066112
§ 371 (c)(1),
(2) Date: May 21, 2014

(87) PCT Pub. No.: WO2013/078230
PCT Pub. Date: May 30, 2013

(65) Prior Publication Data
US 2014/0341933 A1 Nov. 20, 2014

Related U.S. Application Data

(60) Provisional application No. 61/563,273, filed on Nov. 23, 2011, provisional application No. 61/564,174, filed on Nov. 28, 2011.

(51) Int. Cl.
*C12N 5/10* (2006.01)
*C12N 5/0783* (2010.01)

(52) U.S. Cl.
CPC ...... *C12N 5/0637* (2013.01); *C12N 2501/998* (2013.01); *C12N 2502/99* (2013.01); *C12N 2506/11* (2013.01)

(58) Field of Classification Search
None
See application file for complete search history.

(56) References Cited

U.S. PATENT DOCUMENTS

| | | |
|---|---|---|
| 5,350,674 A | 9/1994 | Boenisch et al. |
| 5,585,362 A | 12/1996 | Wilson et al. |
| 5,626,561 A | 5/1997 | Butler et al. |
| 5,787,900 A | 8/1998 | Butler et al. |
| 5,843,069 A | 12/1998 | Butler et al. |
| 5,902,745 A | 5/1999 | Butler et al. |
| 5,913,998 A | 6/1999 | Butler et al. |
| 5,980,889 A | 11/1999 | Butler et al. |
| 6,326,193 B1 | 12/2001 | Liu et al. |
| 2003/0147869 A1* | 8/2003 | Riley ............... C12N 5/0634 424/93.21 |
| 2003/0224520 A1* | 12/2003 | June ............... C12N 5/0634 435/455 |
| 2004/0101519 A1 | 5/2004 | June et al. |
| 2006/0034810 A1 | 2/2006 | Riley et al. |
| 2011/0268752 A1 | 11/2011 | Riley et al. |

FOREIGN PATENT DOCUMENTS

| | | |
|---|---|---|
| WO | WO0129058 | 4/2001 |
| WO | WO0196584 | 12/2001 |
| WO | WO03057171 | 7/2003 |
| WO | WO2011/060218 | 5/2011 |

OTHER PUBLICATIONS

Beissert et al., Journal of Investigative Dermatology (2006) 126, 15-24.*
Huang (Pharmacology and Therapeutics, 2000, 86: 201-215.*
Abrahamsen, et al., "Stimulatory effect of counterflow centrifugal elutriation in large-scale separation of peripheral blood monocytes can be reversed by storing the cells at 37 degrees C." 1991, J Clin Apher 6:48-53 (Abstract).
Afkarian, et al., "T-bet is a STAT1-induced regulator of IL-12R expression in naïve CD4+ T cells." 2002, Nat Immunol 3:549-557 (Abstract).
Amarnath et al., "The PDL1-PD1 axis converts human TH1 cells into regulatory T cells." Sci Transl Med, 3(111):1-13 (2011).
Amarnath, et al., "Rapamycin generates anti-apoptotic human Th1/Tc1 cells via autophagy for induction of xenogeneic GVHD." 2010, Autophagy 6(4):523-41.
Amarnath, et al., "Regulatory T cells and human myeloid dendritic cells promote tolerance via programmed death ligand-1." 2010, PLoS Biol 8(2):e1000302.
Bending, et al., 2009, "Highly purified Th17 cells from BDC2.5NOD mice convert into Th1-like cells in NOD/SCID recipient mice." J Clin Invest 119(3):565-72.

(Continued)

*Primary Examiner* — Ilia Ouspenski
(74) *Attorney, Agent, or Firm* — Saul Ewing LLP; Kathryn Doyle

(57) ABSTRACT

The present invention provides methods and compositions for converting a T cell into a cell that exhibits at least one regulatory T cell phenotype. The converted T cell is generated by contacting a T cell with a cell that is modified to comprise an agent capable of activating PD1 signaling in a T cell. The converted T cell is useful for preventing, suppressing, blocking or inhibiting an immune response. For example the converted T cell is useful for preventing rejection of a transplanted tissue in a human or other animal host, or protecting against graft versus host disease. The converted T cell can also be used to treat autoimmune diseases.

6 Claims, 25 Drawing Sheets

(56) References Cited

OTHER PUBLICATIONS

Bird et al., "Single-chain antigen-binding proteins." 1988, Science 242:423-426.
Blazar, et al., "Blockade of programmed death-1 engagement accelerates graft-versus-host disease lethality by an IFN-gamma-dependent mechanism." 2003, J Immunol 171:1272-1277.
Butte, et al., "Programmed death-1 ligand 1 interacts specifically with the B7-1 costimulatory molecule to inhibit T cell responses." 2007, Immunity 27:111-122.
Caretto, et al., "Cutting edge: the Th1 response inhibits the generation of peripheral regulatory T cells." 2010, J Immunol 184:30-34.
Chemnitz, et al., "SHP-1 and SHP-2 associate with immunoreceptor tyrosine-based switch motif of programmed death 1 upon primary human T cell stimulation, but only receptor ligation prevents T cell activation." 2004, J Immunol 173:945-954.
Chen, et al., "Discovery of a novel shp2 protein tyrosine phosphatase inhibitor." 2006, Mol Pharmacol 70:562-570.
Chen, et al., "Blockade of interleukin-6 signaling augments regulatory T-cell reconstitution and attenuates the severity of graft-versus-host disease." 2009, Blood 114:891-900.
Egen, et al., "CTLA-4: new insights into its biological function and use in tumor immunotherapy." 2002, Nat Immunol 3:611-618 (Abstract).
Fife, et al., "Interactions between PD-1 and PD-L1 promote tolerance by blocking the TCR-induced stop signal." 2009, Nat Immunol 10:1185-1192 (Abstract).
Fiorentino, et al., "Two types of mouse T helper cell. IV. Th2 clones secrete a factor that inhibits cytokine production by Th1 clones." 1989, J Exp Med 170:2081-2095.
Franceschini, et al., "PD-L1 negatively regulates CD4+CD25+Foxp3+ Tregs by limiting STAT-5 phosphorylation in patients chronically infected with HCV." 2009, J Clin Invest 119:551-564.
Francisco, et al., "PD-L1 regulates the development, maintenance, and function of induced regulatory T cells." 2009, J Exp Med 206:3015-3029.
Francisco, et al., "The PD-1 pathway in tolerance and autoimmunity." 2010, Immunol Rev 236:219-242.
Gobert et al., "Regulatory T cells recruited through CCL22/CCR4 are selectively activated in lymphoid infiltrates surrounding primary breast tumors and lead to an adverse clinical outcome." 2009, Cancer Res 69:2000-2009.
Hegazy, et al., "Interferons direct Th2 cell reprogramming to generate a stable GATA-3(+)T-bet(+) cell subset with combined Th2 and Th1 cell functions." 2010, Immunity 32:116-128.
Holland, 2007, "Interferon gamma, IL-12, IL-12R and STAT-1 immunodeficiency diseases: disorders of the interface of innate and adaptive immunity." Immunol Res 38:342-346 (Abstract).
Huston et al., "Protein engineering of antibody binding sites: recovery of specific activity in an anti-digoxin single-chain Fv analogue produced in *Escherichia coli*." 1988, Proc. Natl. Acad. Sci. USA 85:5879-5883.
Kerkar, et al., "Tumor-specific CD8+ T cells expressing interleukin-12 eradicate established cancers in lymphodepleted hosts." 2010, Cancer Res 70:6725-6734.
Kline and Gajewski, "Clinical development of mAbs to block the PD1 pathway as an immunotherapy for cancer." 2010, Curr Opin Investig Drugs 11:1354-1359 (Abstract).
Koenen, et al., "Human CD25highFoxp3pos regulatory T cells differentiate into IL-17-producing cells." 2008, Blood 112:2340-2352.
Latchman, et al., "PD-L2 is a second ligand for PD-1 and inhibits T cell activation." 2001, Nat Immunol 2:261-268; (Abstract).
Lee, et al., "Blocking the monocyte chemoattractant protein-1/CCR2 chemokine pathway induces permanent survival of islet allografts through a programmed death-1 ligand-1-dependent mechanism." 2003, J Immunol 171:6929-6935.

Lee, et al., "Late developmental plasticity in the T helper 17 lineage." 2009, Immunity 30:92-10.
Lighvani, et al., "T-bet is rapidly induced by interferon-gamma in lymphoid and myeloid cells." 2001, Proc Natl Acad Sci U S A 98:15137-15142.
Lu, et al., "Function of miR-146a in controlling Treg cell-mediated regulation of Th1 responses." 2010, Cell 142:914-929.
Ma et al., "PD-1 negatively regulates interleukin-12 expression by limiting STAT-1 phosphorylation in monocytes/macrophages during chronic hepatitis C virus infection." 2011 Immunology 132(3):421-31.
Mariotti et al., "Graft rejection as a Th1-type process amenable to regulation by donor Th2-type cells through an interleukin-4/STAT6 pathway." 2008, Blood 112:4765-4775.
Martin-Orozco, et al., "Th17 cells promote pancreatic inflammation but only induce diabetes efficiently in lymphopenic hosts after conversion into Th1 cells." 2009, Eur J Immunol 39:216-224.
Mueller, et al., "PD-L1 has distinct functions in hematopoietic and nonhematopoietic cells in regulating T cell responses during chronic infection in mice." 2010, J Clin Invest 120:2508-2515.
Mukasa, et al., "Epigenetic instability of cytokine and transcription factor gene loci underlies plasticity of the T helper 17 cell lineage." 2010, Immunity 32:616-627.
Mullen, et al., "Role of T-bet in commitment of TH1 cells before IL-12-dependent selection." 2001, Science 292:1907-1910.
Ohigashi, et al., "Clinical significance of programmed death-1 ligand-1 and programmed death-1 ligand-2 expression in human esophageal cancer." 2005, Clin Cancer Res 11:2947-2953.
Ohtani, et al., "Dissection of signaling cascades through gp130 in vivo: reciprocal roles for STAT3- and SHP2-mediated signals in immune responses." 2000, Immunity 12:95-105.
O'Shea and Paul, "Mechanisms underlying lineage commitment and plasticity of helper CD4+ T cells." 2010, Science 327:1098-1102.
Ramsdell, et al., "Differential ability of Th1 and Th2 T cells to express Fas ligand and to undergo activation-induced cell death." 1994, Int Immunol 6:1545-1553 (Abstract).
Robbins, et al., "Tumor regression in patients with metastatic synovial cell sarcoma and melanoma using genetically engineered lymphocytes reactive with NY-ESO-1." 2011, J Clin Oncol 29:917-924.
International Search Report and Written Opinion for PCT/US2012/066112 dated Feb. 5, 2013.
Sharma et al., "Plasmacytoid dendritic cells from mouse tumor-draining lymph nodes directly activate mature Tregs via indoleamine 2,3-dioxygenase." 2007, J Clin Invest 117:2570-2582.
Sher, et al., "Production of IL-10 by CD4+ T lymphocytes correlates with down-regulation of Th1 cytokine synthesis in helminth infection." 1991, J Immunol 147:2713-2716 (Abstract).
Song, et al., "NSC-87877, inhibitor of SHP-1/2 PTPs, inhibits dual-specificity phosphatase 26 (DUSP26)." 2009, Biochem Biophys Res Commun 381:491-495 (Abstract).
Tatsumi, et al., "Disease-associated bias in T helper type 1 (Th1)/Th2 CD4(+) T cell responses against MAGE-6 in HLA-DRB10401(+) patients with renal cell carcinoma or melanoma." 2002, J Exp Med 196:619-628.
Ui-Tei et al., "Sensitive assay of RNA interference in *Drosophila* and Chinese hamster cultured cells using firefly luciferase gene as target." 2000 FEBS Letters 479: 79-82.
Yang, et al., "Molecular antagonism and plasticity of regulatory and inflammatory T cell programs." 2008, Immunity 29:44-56.
Yoshimitsu, et al., "Bioluminescent imaging of a marking transgene and correction of Fabry mice by neonatal injection of recombinant lentiviral vectors." 2004, Proc Natl Acad Sci U S A 101:16909-16914.
D'Addio et al., "The Link between the PDL1 Costimulatory Pathway and Th17 Fetomaternal Tolerance." 2011, J Immunol 187(9):4530-41.
Hippen et al., "Generation and Large-Scale Expansion of Human Inducible Regulatory T Cells that Suppress Graft-Versus-Host Disease." 2011, Am J Transplant 11(6):1148-57.

(56) References Cited

OTHER PUBLICATIONS

Kline et al., "Clinical development of mAbs to block the PD1 pathway as an immunotherapy for cancer." 2010 Curr Opin Investig Drugs 11(12):1354-1359.
Wang, et al., "PD1 blockade reverses the suppression of melanoma antigen-specific CTL by $CD4^+CD25^{HI}$ regulatory T cells." 2009, International Immunology 21(9):1065-77.
European extended search report for EP 12851070 dated Oct. 14, 2015.

* cited by examiner

SEQUENCE LISTING

```
<160> NUMBER OF SEQ ID NOS: 2

<210> SEQ ID NO 1
<211> LENGTH: 873
<212> TYPE: DNA
<213> ORGANISM: Artificial
<220> FEATURE:
<223> OTHER INFORMATION: Chemically synthesized

<400> SEQUENCE: 1
atgaggatat ttgctgtctt tatattcatg acctactggc atttgctgaa cgcatttact      60
gtcacggttc ccaaggacct atatgtggta gagtatggta gcaatatgac aattgaatgc     120
aaattcccag tagaaaaaca attagacctg gctgcactaa ttgtctattg ggaaatggag     180
gataagaaca ttattcaatt tgtgcatgga gaggaagacc tgaaggttca gcatagtagc     240
tacagacaga gggcccggct gttgaaggac cagctctccc tgggaaatgc tgcacttcag     300
atcacagatg tgaaattgca ggatgcaggg gtgtaccgct gcatgatcag ctatggtggt     360
gccgactaca agcgaattac tgtgaaagtc aatgccccat acaacaaaat caaccaaaga     420
attttggttg tggatccagt cacctctgaa catgaactga catgtcaggc tgagggctac     480
cccaaggccg aagtcatctg gacaagcagt gaccatcaag tcctgagtgg taagaccacc     540
accaccaatt ccaagagaga ggagaagctt ttcaatgtga ccagcacact gagaatcaac     600
acaacaacta atgagatttt ctactgcact tttaggagat tagatcctga ggaaaaccat     660
acagctgaat tggtcatccc agaactacct ctggcacatc ctccaaatga aaggactcac     720
ttggtaattc tgggagccat cttattatgc cttggtgtag cactgacatt catcttccgt     780
ttaagaaaag ggagaatgat ggatgtgaaa aaatgtggca tccaagatac aaactcaaag     840
aagcaaagtg atacacattt ggaggagacg taa                                  873

<210> SEQ ID NO 2
<211> LENGTH: 290
<212> TYPE: PRT
<213> ORGANISM: Artificial
<220> FEATURE:
<223> OTHER INFORMATION: Chemically synthesized

<400> SEQUENCE: 2

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30
```

```
Gly Ser Asn Met Thr Ile Glu Cys Lys Phe Pro Val Glu Lys Gln Leu
        35              40              45
Asp Leu Ala Ala Leu Ile Val Tyr Trp Glu Met Glu Asp Lys Asn Ile
    50              55              60
Ile Gln Phe Val His Gly Glu Glu Asp Leu Lys Val Gln His Ser Ser
65              70              75              80
Tyr Arg Gln Arg Ala Arg Leu Leu Lys Asp Gln Leu Ser Leu Gly Asn
            85              90              95
Ala Ala Leu Gln Ile Thr Asp Val Lys Leu Gln Asp Ala Gly Val Tyr
        100             105             110
Arg Cys Met Ile Ser Tyr Gly Gly Ala Asp Tyr Lys Arg Ile Thr Val
        115             120             125
Lys Val Asn Ala Pro Tyr Asn Lys Ile Asn Gln Arg Ile Leu Val Val
    130             135             140
Asp Pro Val Thr Ser Glu His Glu Leu Thr Cys Gln Ala Glu Gly Tyr
145             150             155             160
Pro Lys Ala Glu Val Ile Trp Thr Ser Ser Asp His Gln Val Leu Ser
            165             170             175
Gly Lys Thr Thr Thr Thr Asn Ser Lys Arg Glu Glu Lys Leu Phe Asn
            180             185             190
Val Thr Ser Thr Leu Arg Ile Asn Thr Thr Thr Asn Glu Ile Phe Tyr
        195             200             205
Cys Thr Phe Arg Arg Leu Asp Pro Glu Glu Asn His Thr Ala Glu Leu
        210             215             220
Val Ile Pro Glu Leu Pro Leu Ala His Pro Pro Asn Glu Arg Thr His
225             230             235             240
Leu Val Ile Leu Gly Ala Ile Leu Leu Cys Leu Gly Val Ala Leu Thr
            245             250             255
Phe Ile Phe Arg Leu Arg Lys Gly Arg Met Met Asp Val Lys Lys Cys
            260             265             270
Gly Ile Gln Asp Thr Asn Ser Lys Lys Gln Ser Asp Thr His Leu Glu
            275             280             285
Glu Thr
290
```

USE OF PDL1 EXPRESSING CELLS TO CONVERT T CELLS INTO REGULATORY T CELLS

CROSS-REFERENCE TO RELATED APPLICATIONS

The present application is a 35 U.S.C. §371 national phase application from, and claiming priority to, International Application No. PCT/US2012/066112, filed Nov. 20, 2012, and published under PCT Article 21(2) in English, which claims priority to U.S. Provisional Application Ser. No. 61/563,273, filed Nov. 23, 2011 and 61/564,174, filed Nov. 28, 2011, the contents of which are incorporated by reference herein in their entireties.

STATEMENT REGARDING FEDERALLY SPONSORED RESEARCH OR DEVELOPMENT

This invention was made with government support under P01AI080192 awarded by National Institutes of Health. The government has rights in this invention.

BACKGROUND OF THE INVENTION

CD4+ T-helper (Th) cells of the Th1 phenotype are critical for host protection against tumors (Tatsumi, et al., 2002, J Exp Med 196:619-628) and infections (Holland, 2007, Immunol Res 38:342-346) but must be tightly regulated to promote self-tolerance (Lu, et al., 2010, Cell 142:914-929) and to limit alloimmunity during transplantation therapy (Mariotti et al., 2008, Blood 112:4765-4775). Th1 cells are amenable to regulation by multiple mechanisms, such as FAS-mediated antigen-induced cell death (Ramsdell, et al., 1994, Int Immunol 6:1545-1553) and regulatory T (Treg) cell inhibition (Lu, et al., 2010, Cell 142:914-929). One such mechanism of regulation is differentiation 'plasticity' among Th cell subsets, with functional subset inter-conversion depending on the cytokine micro-environment (O'Shea and Paul, 2010, Science 327:1098-1102). Such plasticity, which has primarily been studied in murine T cells, is most prevalent for Treg and Th17 subsets: Treg cells can morph into Th17 cells upon IL-1 or IL-6 receptor signaling and subsequent STAT3 activation (Koenen, et al., 2008, Blood 112:2340-2352; Yang, et al., 2008, Immunity 29:44-56), and Th17 cells can switch into a Th1 phenotype under the influence of IL-12 signaling and subsequent STAT4 activation (Mukasa, et al., 2010, Immunity 32:616-627).

In contrast, the Th1/Th2 subsets are relatively fixed in their differentiation status (O'Shea and Paul, 2010, Science 327:1098-1102); nonetheless, counter-regulatory cytokines have long been known to promote Th1 to Th2 conversion (Sher, et al., 1991, J Immunol 147:2713-2716) or Th2 to Th1 shifts (Fiorentino, et al., 1989, J Exp Med 170:2081-2095) by activating specific transcription factors. Although STAT4 activation is required for initial Th1 polarization (Mullen, et al., 2001, Science 292:1907-1910), STAT1 activation through IFN-α or IFN-γ receptor signaling appears to be the major contributor to Th1 cell stability through promotion of TBET transcription factor expression (Lighvani, et al., 2001, Proc Natl Acad Sci USA 98:15137-15142; Afkarian, et al., 2002, Nat Immunol 3:549-557).

Recently, the PD1/PDL1 pathway has emerged as a central player in immune regulation (Francisco, et al., 2010, Immunol Rev 236:219-242). Cancer cells that express PDL1 (also known as B7-H1) promote tumor progression through inhibition of PD1-expressing immune effectors (Ohigashi, et al., 2005, Clin Cancer Res 11:2947-2953); in addition, PDL1 modulates cell-mediated immunity in the infectious disease setting (Mueller, et al., 2010, J Clin Invest 120:2508-2515). Furthermore, allogeneic effector T cell responses are susceptible to PD1 pathway modulation, as evidenced in models of graft-versus-host disease (GVHD) (Blazar, et al, 2003, J Immunol 171:1272-1277) and graft rejection (Lee, et al., 2003, J Immunol 171:6929-6935).

PD1/PDL1 interactions have been characterized previously to inhibit T cell receptor (TCR) signaling by recruiting the SHP-1 and SHP-2 (SHP1/2) phosphatases, which interfere with TCR signaling (Chemnitz, et al., 2004, J Immunol 173:945-954) and induce a TCR stop signal that limits T cell interactions with dendritic cells (DC) (Fife, et al., 2009, Nat Immunol 10:1185-1192). Such immune modulation mechanisms are not specific for Th1 cells: For example, PD1 activation inhibits the suppressor function of Treg cells (Franceschini, et al., 2009, J Clin Invest 119:551-564) and impairs monocyte immunity (Ma et al., 2011 Immunology 132(3):421-31) in humans infected with hepatitis C. In addition to such direct mechanisms of T cell anergy, PDL1 also indirectly modulates T cells by inducing plasmacytoid DCs, which increase Treg cell numbers and result in Treg cell suppression of anti-tumor responses in a PDL1-dependent manner (Sharma et al., 2007, J Clin Invest 117:2570-2582). This DC/Treg cell biology can be bi-directional, as human PDL1-expressing Tregs condition monocytes to express PDL1 and suppress cell-mediated immunity (Amarnath, et al., 2010, PLoS Biol 8:e1000302). Furthermore, PD1 activation of naïve T cells favors inducible Treg formation by promoting phosphatase and tensin homolog (PTEN) expression and limiting downstream mTOR activation (Francisco, et al., 2009, J Exp Med 206:3015-3029).

There have been no reports in the literature to suggest that PD1/PDL1 interactions play a special role in the modulation of Th1 cell plasticity. There remains a need in the art for compositions and methods of differentiating Th1 cells. The present invention fills this need in the art.

SUMMARY OF THE INVENTION

The invention provides a method of converting a T cell into a cell that exhibits a regulatory T cell phenotype. In one embodiment, the method comprises contacting a T cell with a K562 cell modified to comprise an agent capable of activating PD1 signaling in the T cell thereby converting the T cell into a cell that exhibits a regulatory T cell phenotype.

In one embodiment, the agent is selected from the group consisting of PDL1, PDL2, PD1 ligand, and an anti-PD1 antibody.

In one embodiment, the T cell prior to contacting with the K562 cell modified to comprise an agent capable of activating PD1 signaling, is a non-regulatory T cell selected from the group consisting of a CD4$^+$ cell, a CD4$^+$CD25$^-$ cell, a CD4$^+$CD25$^-$45 RA$^+$ cell, and any combination thereof.

In one embodiment, the T cell prior to contacting with the K562 cell modified to comprise an agent capable of activating PD1 signaling is selected from the group consisting of a Th1 cell, a Th2 cell, a Th17 cell, and any combination thereof.

In one embodiment, the converted regulatory T cell exhibits a phenotype selected from the group consisting of expression of Foxp3, suppression of effector T cell activation, and any combination thereof.

In one embodiment, the K562 cell modified to comprise an agent capable of activating PD1 signaling is irradiated.

The invention also provides a converted T cell produced by a method comprising contacting a T cell with a K562 cell modified to comprise an agent capable of activating PD1 signaling in the T cell thereby converting the T cell.

The invention also provides a method for inhibiting alloreactive T cells, the method comprising contacting the alloreactive T cells with an effective amount of a converted regulatory T cell (Treg). In one embodiment, a Treg is produced by a method of contacting a T cell with a K562 cell modified to comprise an agent capable of activating PD1 signaling in the T cell thereby converting the T cell into a cell that exhibits a regulatory T cell phenotype.

The invention also provides a method for inhibiting cytotoxic T-lymphocyte (CTL) activity, the method comprising contacting a cytotoxic T-lymphocyte with an effective amount of a converted Treg. In one embodiment, a Treg is produced by a method of contacting a T cell with a K562 cell modified to comprise an agent capable of activating PD1 signaling in the T cell thereby converting the T cell into a cell that exhibits a regulatory T cell phenotype.

The invention also provides a method for generating an immunosuppressive effect in a mammal having an alloresponse or autoimmune response, the method comprising administering to the mammal an effective amount of a cell population, wherein the cell population comprises a cell selected from the group consisting of a K562 cell modified to comprise an agent capable of activating PD1 signaling in a T cell thereof thereby generating an immunosuppressive effect in the mammal.

The invention provides a method for preventing an allo-response or an autoimmune response in a mammal, the method comprising administering to said mammal, an effective amount of a cell population, wherein said cell population comprises a K562 cell modified to comprise an agent capable of activating PD1 signaling in a T cell thereby preventing said response in said mammal.

The invention provides a method of treating a transplant recipient to reduce in the recipient an immune response against the transplant, the method comprising administering to a transplant recipient, an effective amount of a cell population, wherein said cell population comprises a K562 cell modified to comprise an agent capable of activating PD1 signaling in a T cell thereby reducing an immune response against the antigen.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising FIG. 1A is an image depicting the percentage of IFN-γ secreting human T cells 5 days after adoptive transfer. FIG. 1B is an image depicting that the absolute number of post-transplant splenic IFN-γ$^+$ human T cells was quantified for each cohort. FIG. 1C is an image demonstrating that recipients were challenged with LPS; serum was harvested after 90 min and evaluated for TNF-α content. FIG. 1D is an image demonstrating that cohorts of host mice received the human cell inocula specified, followed by LPS administration at day 5 after transfer to induce lethal cytokine-mediated xGVHD (n, number per cohort: M, ×10$^6$). FIG. 1E is an image depicting a survival curve after xGVHD induction (* indicates p≤0.05; *** indicates p≤0.005).

FIG. 2, comprising FIGS. 2A though 2I, is a series of images demonstrating that PDL-1 modulation occurs in highly purified, ex vivo generated Th1 cells and in vivo-derived pathogenic human Th1 cells.

FIG. 3, comprising FIG. 3A is an image demonstrating that human Th1 cells were expanded ex vivo. Prior to adoptive transfer, Th1 cells were evaluated by intracellular flow cytometry for transcription factor expression and cytokine content. FIG. 3B is an image demonstrating that prior to adoptive transfer, transduced human T cells were evaluated for PDL1 expression (non-transduced cells; PDL1-transduced cells). FIG. 3C is an image demonstrating that NSG mice were injected with Th1 cells (1×10$^6$) alone or with PDL1-transduced T cells (5×10$^4$). Human T cell splenic engraftment for recipients of Th1 cells plus PDL1-transduced cells is shown at day 6 and day 90 after transfer. FIG. 3D is an image depicting TBET expression measured by intracellular flow cytometry in cohorts that received Th1 cells alone, Th1 cells plus control LV-transduced T cells, or Th1 cells plus PDL1-LV transduced T cells. Right panel shows pooled data for TBET expression for each cohort. FIG. 3E is an image depicting that FOXP3 expression was monitored by i.e. flow cytometry at day 6 after transplant in cohorts that received Th1 cells alone, Th1 cells plus control LV-transduced T cells, or Th1 cells plus PDL1-LV transduced T cells. Right panel shows pooled data for FOXP3 expression for each cohort. FIG. 3F is an image demonstrating TBET and FOXP3 expression at day 90 after transplant in recipients of Th1 cells or Th1 cells plus PDL1-expressing T cells. FIG. 3G is an image of a survival curve for recipients of Th1 cells alone or Th1 cells plus PDL1-expressing T cells. (* indicates $p \leq 0.05$, ** indicates $p \leq 0.005$).

FIG. 4, comprising FIG. 4A is an image depicting that at day 6, absolute numbers of human T cells (left panel) and PD1-expressing T cells (right panel) were enumerated in the spleen. FIG. 4B is an image demonstrating that splenocytes were stimulated (PMA/ionomycin) and the number of FOXP3-negative T cells expressing IFN-γ, IL-2 and TNF-α were quantified; conversely, the number of FOXP3-positive T cells deficient in production of IFN-γ, IL-2, and TNF-α were quantified. FIG. 4C is an image demonstrating that recipients were challenged with LPS and serum was harvested 90 min later for measurement of TNF-α. FIG. 4D is an image demonstrating that absolute numbers of engrafted human T cells expressing TBET were quantified. FIG. 4E is an image demonstrating that cohorts of host mice received the human cell inocula specified, followed by LPS administration on day 5 after transfer for assessment of lethal cytokine-mediated xGVHD (n, number per cohort). Data panels represent n=10 replicates per cohort (* indicates $p \leq 0.05$, ** indicates $p \leq 0.005$).

FIG. 5, comprising FIG. 5A is an image demonstrating that at day 6, absolute numbers of human T cells engrafted in the spleen were enumerated. FIG. 5B is an image demonstrating that splenocytes were stimulated (PMA/ionomycin) and the number of FOXP3-negative T cells expressing IFN-γ, IL-2, or TNF-α were quantified; conversely, the number of FOXP3-positive T cells deficient in production of IFN-γ, IL-2, and TNF-α were quantified. FIG. 5C is an image demonstrating that recipients were challenged with LPS and serum was harvested 120 min later for measurement of TNF-α. FIG. 5D is an image demonstrating that absolute numbers of engrafted human T cells expressing TBET were quantified. FIG. 5E is an image demonstrating that cohorts of host mice received the human cell inocula specified, followed by LPS administration on day 5 after transfer for assessment of lethal cytokine-mediated xGVHD (n, number per cohort). Data panels represent n=10 replicates per cohort (* indicates $p \leq 0.05$, ** indicates $p \leq 0.005$).

FIG. 6, comprising FIG. 6A is a schematic of a working model for Th1 cell plasticity: (1) PDL1/PD1 interactions recruit SHP1/2; (2) SHP1/2 inactivates STAT1, thereby abrogating IFN-mediated maintenance of TBET; (3) STAT1 inhibits FOXP3. To investigate aspects of this model, Th1 cells were restimulated in the presence of IFN-γ or IL-6 for 30 min prior to phospho-flow cytometry. Representative examples shown are Th1 cells without additional cytokine addition either alone or with PDL1-coated beads; Th1 cells plus a STAT1 activating cytokine (IFN-γ) alone or with PDL1-coated beads; and Th1 cells plus a STAT3 activating cytokine (IL-6) alone or with PDL1-coated beads (FIG. 6B). FIG. 6C is an image demonstrating that nuclear lysates of Th1 cells were obtained (n=5 donors) and subjected to an ELISA-based STAT activation assay. STAT1 activation was evaluated in the presence of PDL1 (top left panel) or PDL1 plus the SHP1/2 inhibitor NSC87877 (top right panel); STAT3 activation was evaluated in the presence of PDL1 (bottom left panel) or PDL1 plus NSC87877 (bottom right panel). FIG. 6D is an image demonstrating that Th1 cells were evaluated for TBET expression in the presence or absence of PDL1. FIG. 6E is an image demonstrating that Th1 cells were evaluated for demethylation status of the FOXP3 TSDR locus. For each panel: * indicates $p \leq 0.05$,  indicates $p \leq 0.005$, * indicates $p \leq 0.0005$).

FIG. 7 comprising FIG. 7A is a schematic demonstrating that control-LV construct encodes expression of TMPK.CD19 fusion protein using EF-1a promoter (top panel); therapeutic-LV construct also encodes PDL1 after an IRES sequence (bottom panel). FIG. 7B is an image demonstrating post-transduction co-expression of PDL1 and fusion protein. Non-transduced cells expressed CD4 in the absence of CD19 and PDL1 (top and bottom left panels). Control-LV transduced cells expressed CD19 (top and bottom middle panels). PDL1-LV transduced cells co-expressed CD19 and PDL1 (top and bottom right panels). Pooled results from n=7 normal donors are shown. FIG. 7C is an image of representative flow plots showing in vivo transgene expression. Transduced cells were enriched by flow sorting and adoptively transferred to rag2−/−cγ−/− hosts; FIG. 7D shows the absolute number of transgene-expressing cells that was quantified at day 5 post-transfer in spleen (left panel) and bone marrow (right panel) (NT, non-transduced; T, therapeutic-LV transduced; pooled results, n=5 per cohort). Harvested T cells were co-stimulated ex vivo and expanded for 5 days to assess transgene expression stability of cells harvested from spleen (bottom panel) and bone marrow (bottom panel). FIG. 7E is an image demonstrating persistent in vivo transgene expression. Transduced and enriched human T cells were adoptively transferred; transgene-expressing cells were quantified at day 20 post-transfer in spleen (top left panel) and bone marrow (top right panel). Harvested T cells were co-stimulated ex vivo and expanded for 7 days and transgene expression was determined on cells harvested from spleen (bottom left panel) and bone marrow (bottom right panel). For each panel, n=5 per cohort unless otherwise indicated; * indicates $p \leq 0.05$.

FIG. 8, comprising FIG. 8A is an image of representative plots showing eGFP expression (top panel), and cell death markers in eGFP-negative (bottom left panel) and eGFP-positive (bottom right panel) cells. FIG. 8B is an image of representative plots showing CD19 expression (top panel), and cell death markers in CD19-negative (bottom left panel) and CD19-positive (bottom right panel) cells. FIG. 8C is an image showing that PDL1-LV-transduced T cells exposed to AZT ex vivo lack engraftment potential. Transduced T cells were exposed to AZT (100 μM; three days); live cells were then sorted and adoptively transferred to NOD/SCID hosts to determine engraftment potential (at day 5 post-transfer). Engraftment of PDL1-LV-transduced T cells not exposed to AZT was compared to engraftment of non-transduced or eGFP-transduced T cells exposed to AZT (left panel); engraftment of PDL1-LV transduced T cells either exposed or not exposed to AZT ex vivo (right panel). FIG. 8D is an image showing that T cells transduced with PDL1-LV were adoptively transferred to NOD/SCID hosts that received AZT therapy (top left panel) (50 mg/kg/d; twice per, absolute number of splenic T cells engrafted was determined for recipients (n=5 per cohort) of PDL1.TMPK transduced T cells with or without in vivo AZT treatment (bottom left panel) and PDL1.TMPK-transduced T cells with or without AZT treatment (bottom right panel). For each panel, * indicates p≤0.05.

FIG. 9, comprising FIG. 9A is an image showing that Th1 cell splenic engraftment at 24 hr post-infusion (left panel, representative data; right panel, pooled data of n=3 per cohort). In vivo plasticity of Th1 cells was monitored by assessment of cytokine secretion and FOXP3 expression by i.e. flow cytometry. Absolute numbers of splenic Th1 cells expressing IFN-γ were quantified (FIG. 9B); Th1 cells expressing FOXP3 in the absence of IFN-γ were also enumerated (FIG. 9C). (* indicates p≤0.05).

FIG. 10, comprising FIG. 10A is an image demonstrating that at day 5 post transfer, splenocytes were harvested and Th1 cells were characterized for co-inhibitory molecules, such as B7H4 (left panel) and HVEM (right panel). FIG. 10B is an image demonstrating that splenocytes were stimulated ex vivo with PMA and ionomycin for 4 hrs and cytokine production was measured using flow cyometry. Absolute numbers of IFN-γ-FOXP3+, IL2-FOXP3+, TNF-FOXP3+, IL2+FOXP3− and TNF+FOXP3− are shown. Human pathogenic Th1 cells were utilized in an additional in vivo experiment along with CD4+ T cells expressing PDL1 or CD8+ T cells expressing PDL1. FIG. 10C is an image demonstrating that at day 5 post transfer, splenocytes were harvested and absolute numbers of hB7H4 (left panel) and hHVEM (right panel) were quantified. FIG. 10D is an image depicting absolute numbers of IFN-γ-FOXP3+, IL2+FOXP3−, IL2-FOXP3+, TNF-FOXP3+ and TNF+FOXP3−. FIG. 10E is an image demonstrating that using the same pathogenic Th1 cells, another transplant was performed where irradiated K562 cells (K) or K562 cells expressing PDL1 (K.PDL1) were adoptively transferred. At day 5 after transfer, splenocytes were harvested and absolute numbers of hB7H4 (left panel) and hHVEM (right panel) is shown. FIG. 10F is an image demonstrating that absolute numbers of IFN-γ-FOXP3+, IL2+FOXP3−, IL2-Foxp3+, TNF+FOXP3− and TNF-FOXP3+ were quantified. * indicates p≤0.05, ** indicates p≤0.005.

FIG. 11, comprising FIGS. 11A though 11F, is a series of images demonstrating the evaluation of reverse signaling in vitro and in vivo during exposure to Th1 cells. Human CD4+ and CD8+ T cells were transduced with either GFP LV or PDL1 LV.

FIG. 12, comprising FIG. 12A is an image demonstrating that STAT1 signaling of the Th1 cells after co-culture was measured (left panel). STAT1 signaling on LV transduced T cells was also measured before co-culture (middle panel) and after co-culture (right panel). FIG. 12B is an image demonstrating that STAT4 signaling was also measured in Th1 cells following co-culture (left panel) and on LV transduced T cells were also measured before co-culture (middle panel) and after co-culture (right panel). FIG. 12C is an image demonstrating that Th1 cells were also characterized for PDL1 binding ligands PD1 (left panel) and CD80 (right panel) following co-culture. FIG. 12D is an image demonstrating that at day 3, after co-culture, Th1 cells were restimulated and flow cytometry was performed to measure expression of TBET (left panel) and IFN-γ (right panel). FIG. 12E is an image demonstrating that in order to detect TGF-β signaling, Th1 cells were either stimulated with beads coated with antibodies to CD3 and CD28 alone or in the presence of PDL1 coated beads or with rhTGF-β for 6 hrs. Protein lysates were prepared after 6 hrs and western blotting analysis was performed to detect p-smad2 signaling. Representative blots from 2 donors are shown along with total Smad2 protein expression. * indicates p≤0.05, ** indicates p≤0.005.

FIG. 13, comprising FIG. 13A is an image of representative flow cytometry data for control Th1 cells (left panel) and Th1 cells treated with siRNA for PD1 (right panel). FIG. 13B is an image of representative data of PD1 expression of Th1 cells after flow sorting prior to adoptive transfer. FIG. 13C is an image showing Th1 cell SHP1/2 protein expression by western blot analysis with SHP1 or SHP2 siRNA treatment. FIG. 13D is an image demonstrating that untreated Th1 cells, Th1 cells with PD1 knockdown, and Th1 cells treated with SHP1/2 SiRNA (n=5 donors) were evaluated for STAT1 activation. For each panel: * indicates p≤0.05,  indicates p≤0.005, * indicates p≤0.0005).

DETAILED DESCRIPTION OF THE INVENTION

Figures 1A, 1B, 1C:
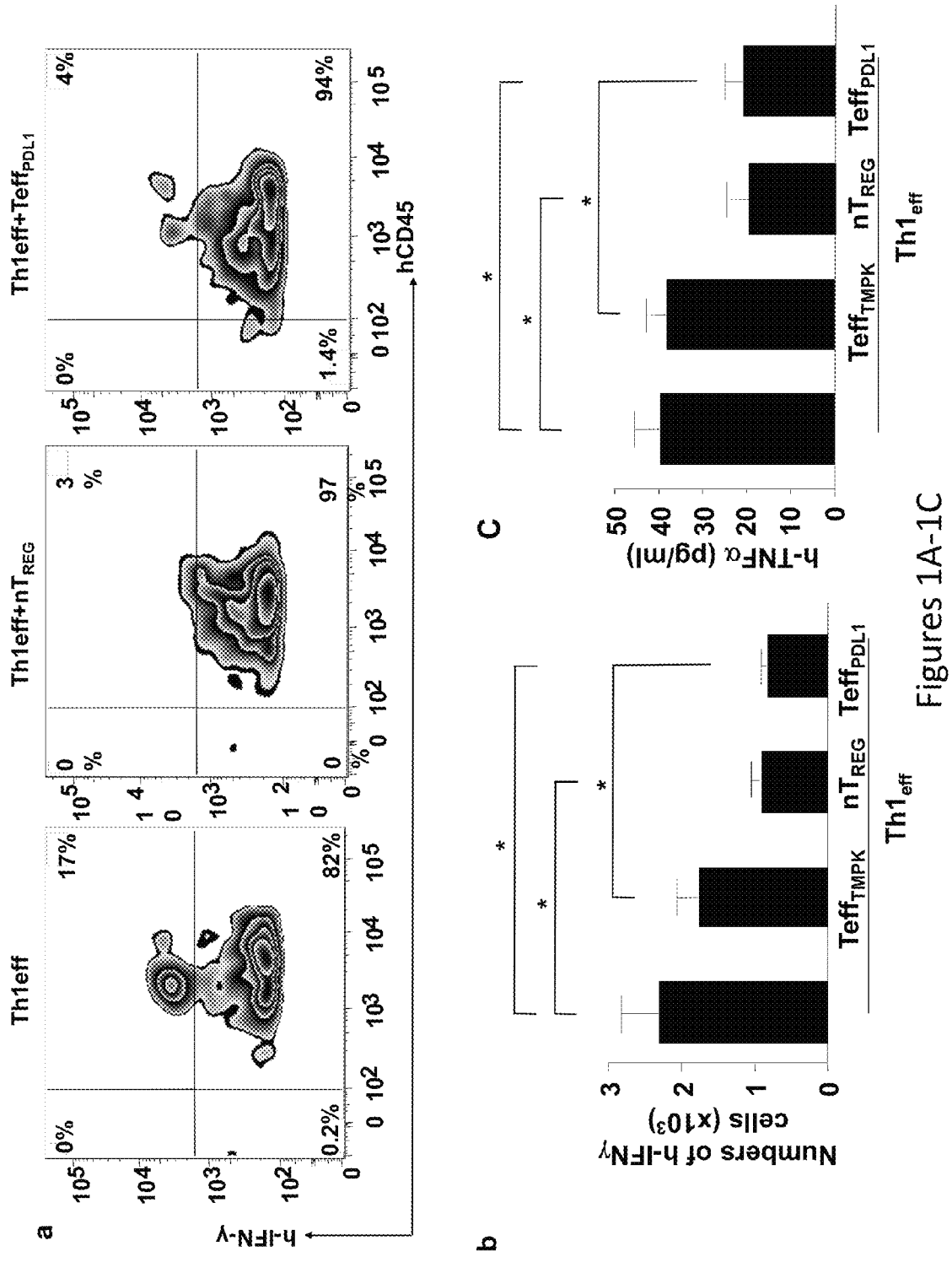
FIGS. 1A through 1E, is a series of images demonstrating that Th1 cell-mediated xGVHD in an LPS Model is prevented by PDL1-expressing effector T cells. Th1 cells were adoptively transferred to rag2$^{-/-}$cγ$^{-/-}$ mice alone or in combination with control-LV transduced T cells, Treg cells, or PDL1-transduced T cells.

The present invention encompasses compositions and methods for modulating T cell differentiation, preferably differentiation of a T cell to a cell that exhibits at least one regulatory T cell phenotype. For example, the invention provides a composition and a method of converting Th1 cells into functional regulatory T cells (Tregs). The converted regulatory T cells of the invention are able to suppress lethality in a xenogeneic model of GVHD.

In one embodiment, a T cell is converted into a regulatory T cell phenotype by way of activating programmed death 1 (PD1) signaling in the T cell. For example, a first cell modified to express a programmed death ligand (PDL) can be used to activate PD1 signaling in a second cell, wherein the second cell is converted to exhibit a regulatory T cell phenotype. In one embodiment, the first cell can be a conventional T cell or a myeloid tumor cell, preferably an irradiated K562 myeloid tumor cell that is modified to overexpress a PDL and the second cell is a Th1 cell. However, the invention should not be limited to a specific cell type with respect to the first cell. Rather, any cell that can be modified to overexpress a PDL and can be contacted with a T cell can be used as the first cell in the invention.

In one embodiment, the present invention is directed to the use of a cell modified to express a PDL (e.g., PDL1 and/or PDL2) to induce or differentiate a naive T cell towards a regulatory T cell phenotype. In one embodiment, the PDL modified cell can be used to convert Th1 cells into Tregs in vivo. Preferably, the converted Tregs express Foxp3 and are able to suppress effector T cell activation.

In one embodiment, the PDL modified cells of the invention are able to deliver signals to a surrounding cell to promote regulatory T cell development and maintenance of regulatory T cell function. For example, a conventional T cell or an irradiated K562 myeloid tumor cell overexpressing PDL1 can be used to convert a Th1 cell into a FOXP3$^+$ regulatory T cell in vivo, thereby preventing human-into-mouse xenogeneic GvHD (xGvHD).

In one embodiment, the PDL modified cells of the invention includes a cell modified to comprise a ligand for PD1 that is localized on its cell surface. This can be accomplished by transfecting a cell with a nucleic acid encoding the ligand for PD1 in a form suitable for its expression on the cell surface or alternatively by coupling a ligand for PD1 to the cell surface. Alternatively, an anti-PD-1 antibody can be "loaded" to the cell surface of a cell. That is, the skilled artisan would understand, based upon the disclosure provided herein, that a cell comprising an antibody can be produced, as exemplified elsewhere herein, by introducing a nucleic acid encoding a human Fcγ receptor (e.g., CD32 or CD64), into the cell. The CD32 and/or CD64 expressed on the cell surface can then be "loaded" with any desired antibody that binds PD1 and activated PD1 on the cell. In one embodiment, the PDL modified cells of the invention does not display exogenous anti-CD3 antibody and/or anti-CD28 antibody on its cell surface.

In addition, the present invention provides a method for enhancing tolerance in a mammalian host to prolong foreign graft survival in the host and for ameliorating inflammatory-related diseases, such as autoimmune diseases, including, but not limited to, autoimmune arthritis, autoimmune diabetes, asthma, septic shock, lung fibrosis, glomerulonephritis, arteriosclerosis, as well as AIDS, and the like. In some instances, the converted Tregs are useful for suppressing an immune response.

The present invention further comprises a method for inhibiting proliferation of a T cell. Such inhibition can occur in vitro or in vivo, preferably in an animal, more preferably in a mammal, even more preferably in a human. This is because, as demonstrated by the data disclosed herein, converted Tregs of the present invention are potent suppressors of T cell proliferation.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "agent", "ligand", or "agent that binds a cell surface moiety", as used herein, refers to a molecule that binds to a defined population of cells. The agent may bind any cell surface moiety, such as a receptor, an antigenic determinant, or other binding site present on the target cell population. The agent may be a protein, peptide, antibody and antibody fragments thereof, fusion proteins, synthetic molecule, an organic molecule (e.g., a small molecule), a carbohydrate, or the like. Within the specification and in the context of T cell stimulation, antibodies and natural ligands are used as prototypical examples of such agents.

The terms "agent that binds a cell surface moiety" and "cell surface moiety", as used herein, are used in the context of a ligand/anti-ligand pair. Accordingly, these molecules should be viewed as a complementary/anti-complementary set of molecules that demonstrate specific binding, generally of relatively high affinity.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

The term "expression" as used herein is defined as the transcription and/or translation of a particular nucleotide sequence driven by its promoter.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous. By way of example, the DNA sequences 5'-ATTGCC-3' and 5'-TATGGC-3' share 50% homology.

As used herein, the term "immune cell" is intended to include, but is not limited to, a cell that is of hematopoietic origin and that plays a role in the immune response. Immune cells include, but are not limited to, lymphocytes, such as B cells and T cells; natural killer cells; and myeloid cells, such as monocytes, macrophages, eosinophils, mast cells, basophils, and granulocytes.

As used herein, the term "immune response" includes, but is not limited to, T cell-mediated and/or B cell-mediated immune responses that are influenced by modulation of T cell costimulation. Exemplary immune responses include B cell responses (e.g., antibody production) T cell responses (e.g., cytokine production, and cellular cytotoxicity) and activation of cytokine responsive cells, e.g., macrophages. As used herein, the term "down-modulation" with reference to the immune response includes a diminution in any one or more immune responses, while the term "up-modulation" with reference to the immune response includes an increase in any one or more immune responses. It will be understood that up-modulation of one type of immune response may lead to a corresponding down-modulation in another type of immune response. For example, up-modulation of the production of certain cytokines (e.g., IL-10) can lead to down-modulation of cellular immune responses.

As used herein, the term "modulate" is meant to refer to any change in biological state, i.e. increasing, decreasing, and the like.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence.

Generally, operably linked DNA sequences are contiguous and, where necessary to join two protein coding regions, in the same reading frame.

The term "subject" is intended to include living organisms in which an immune response can be elicited (e.g., mammals), preferably a human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

Description

The present invention is based on the discovery that PDL1 directly modulates Th1 cell differentiation by promoting a tolerogenic Treg phenotype. In one embodiment, the invention provides a method of converting a T cell into a cell that exhibits at least one regulatory T cell phenotype (e.g., expressing Foxp3 and suppresses effector T cell activation).

In one embodiment, the method includes the steps of contacting a T cell (e.g., a naive T cell, Th1, Th2, or Th17) with a cell modified to express a PDL (e.g., PDL1 and/or PDL2) to induce or differentiate the T cell into a cell that exhibits at least one regulatory T cell phenotype. Preferably, the cell modified to express a PDL is the K562 cell. In some instances, the PDL modified cell is contacted with a naive T cell in the presence of one or both of anti-CD3 antibody and anti-CD28 antibody, one or both of which may optionally be present on a bead. In some instances, the PDL expressed on the cell activates PD1 signaling on the T cell to induce differentiation of the T cell into a cell that exhibits a regulatory T cell phenotype thereby generating a converted T cell of the invention.

Accordingly, the converted T cells of the invention can be used in a clinical setting, for example for ameliorating, preventing and/or treating diseases, symptoms and/or disorders associated with an autoimmune disorder, organ transplant rejection, graft versus host disease or allergic or hypersensitivity response. Diseases, symptoms and/or disorders associated with the autoimmune disorder, organ transplant rejection, graft versus host disease or allergic or hypersensitivity response are known to those of skill in the art.

Sources of T Cells

T helper cells (also known as effector T cells or Th cells) are a sub-group of lymphocytes (a type of white blood cell or leukocyte) that plays an important role in establishing and maximizing the capabilities of the immune system and in particular in activating and directing other immune cells. Different types of Th cells have been identified that originate in outcome of a differentiation process and are associated with a specific phenotype. Following T cell development, matured, naive (meaning they have never been exposed to the antigen to which they can respond) T cells leave the thymus and begin to spread throughout the body. Naive T cells can differentiate into a T-helper 1 (Th1), T-helper 2 (Th2), T-helper 17 (Th17), regulatory T cell (Treg) or natural Treg phenotype (nTregs).

Each of these Th cell types secretes cytokines, proteins or peptides that stimulate or interact with other leukocytes, including Th cells. However, each cell type has a peculiar phenotype and activity that interferes and often conflict with the other.

nTregs are a component of the immune system that suppresses biological activities of other cells associated to an immune response. In particular, nTregs can secrete immunosuppressive cytokines TGF-beta and Interleukin 10, and are known to be able to limit or suppress inflammation.

The present invention is based on the discovery that a T cell (e.g., a naive T cell, Th1, Th2, or Th17) can be converted to a cell that exhibits at least one regulatory T cell phenotype (e.g., expressing Foxp3 and suppresses effector T cell activation).

Prior to converting a cell to exhibit at least one regulatory T cell phenotype according to the methods of the invention, a source of T cells is obtained from a subject. Non-limiting examples of subjects include humans, dogs, cats, mice, rats, and transgenic species thereof. Preferably, the subject is a human. T cells can be obtained from a number of sources, including peripheral blood mononuclear cells, bone marrow, lymph node tissue, spleen tissue, umbilical cord, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll separation. In one preferred embodiment, cells from the circulating blood of an individual are obtained by apheresis or leukopheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood by lysing the red blood cells and depleting the monocytes, for example, by centrifugation through a PERCOLL™ gradient. Alternatively, T cells can be isolated from umbilical cord. In any event, a specific subpopulation of T cells can be further isolated by positive or negative selection techniques.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

PDL Modified Cell

In one embodiment, the present invention is directed to the use of a cell modified to activate PD (e.g., PD1) on a T cell. In another embodiment, the present invention is directed to the use of a cell modified to express a PDL (e.g., PDL1 and/or PDL2) to induce or differentiate a T cell towards a regulatory T cell phenotype. In one embodiment, the PDL modified cell can be used to convert Th1 cells into Tregs. Preferably, the converted Tregs express Foxp3 and are able to suppress effector T cell activation.

In one embodiment, the PDL modified cells of the invention are able to deliver signals to a surrounding cell to promote regulatory T cell development and maintenance of regulatory T cell function. Preferably, the signal is the activation of PD1 on a surrounding T cell. In one embodiment, PD1 activation on a surrounding T cell can be accomplished by contacting the T cell with a cell (e.g., K562) that comprises a molecule capable of activating PD1 on the T cell.

In one embodiment, PD1 activation on a T cell can be accomplished by stimulating PD1 on a T cell. An anti-PD1 antibody can be displayed on a cell. The skilled artisan would understand, based upon the disclosure provided herein, that a cell comprising an antibody can be produced, as exemplified elsewhere herein, by introducing a nucleic acid encoding a human Fcγ receptor (e.g., CD32 or CD64), into the cell and the antibody can be load onto the Fcγ receptor. Thus, the present invention includes a cell transduced with CD32 and/or CD64 and loaded with at least one antibody that specifically binds with PD1. In one embodiment, the cell transduced with CD32 and/or CD64 is not loaded with anti-CD3 and/or anti-CD28 antibodies.

However, the invention should not be limited to anti-PD1 antibody. Rather any agent that can induce stimulation of the PD1 molecule is encompassed by the invention. In addition, binding homologues of a natural ligand, whether native or synthesized by chemical or recombinant technique, can also be used in accordance with the invention. Ligands useful for stimulating PD1 can be used in soluble form, attached to the surface of a cell, or immobilized on a solid phase surface as described herein. Anti-PD1 antibodies or fragments thereof are also useful in stimulating PD1 molecule.

In another embodiment, the invention included conventional T cells or irradiated K562 myeloid tumor cells modified to overexpress PDL1 for converting Th1 cells into FOXP3$^+$ regulatory T cells. The converted cells can prevent human-into-mouse xenogeneic GvHD (xGvHD) in vivo.

Accordingly, the present invention encompasses a cell comprising a vector containing sequences of PDL. In brief summary, the expression of natural or synthetic nucleic acids encoding a PDL is typically achieved by operably linking a nucleic acid encoding the desired PDL polypeptide or portions thereof to a promoter, and incorporating the construct into an expression vector. An exemplary nucleic acid sequence of PDL1 is set forth in SEQ ID NO: 1. The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein. An exemplary amino acid sequence of PDL1 is set forth in SEQ ID NO: 2.

The vectors can be suitable for replication and integration in eukaryotes. Typical cloning vectors contain transcription and translation terminators, initiation sequences, and promoters useful for regulation of the expression of the desired nucleic acid sequence.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., MOLECULAR CLONING: A LABORATORY MANUAL, volumes 1-3 (3$^{rd}$ ed., Cold Spring Harbor Press, NY 2001), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a PDL polypeptide or portions thereof the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., MOLECULAR CLONING: A LABORATORY MANUAL volumes 1-3 (3$^{rd}$ ed., Cold Spring Harbor Press, NY 2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Conversion to Tregs

The present invention provides compositions and methods to activate PD1 signaling in a T cell to convert the T cell into a cell that exhibits at least one regulatory T cell phenotype (e.g., expressing Foxp3 and suppresses effector T cell activation). For example, a first cell modified to express the programmed death ligand-1 (PDL1) or programmed death ligand-2 (PDL2) can be used to activate PD1 signaling in a second cell, wherein the second cell is converted to exhibit a regulatory T cell phenotype. In one embodiment, the first cell is an irradiated K562 myeloid tumor cell that is modified to overexpress a PDL.

In one embodiment, the PDL modified cells of the invention are able to deliver signals to a surrounding neighboring cell to promote regulatory T cell development and maintenance of regulatory T cell function. In one embodiment, a neighboring cell can be a Th1 cell. In another embodiment, the neighboring cell can be a T cell that is associated with inflammation. In yet another embodiment, the neighboring cell is a Th17 cell.

In one embodiment, a T cell can be converted into a cell that exhibits a regulatory T cell phenotype by contacting a PDL modified cell of the invention with a T cell. In one exemplary embodiment, a method of ex vivo T cell conversion is provided including the steps of isolating a T cell and contacting the T cell with a PDL modified cell of the invention. In another embodiment, a method of in vivo cell conversion is provided including the steps of administering a PDL modified cell of the invention into a mammal and contacting the administered PDL modified cell with a T cell in a mammal wherein the T cell differentiates into a cell that exhibits at least one regulatory T cell phenotype.

In the context of ex vivo T cell conversion, the converted T cell may be maintained in culture and/or expanded. In certain exemplary embodiments, T cell conversion is performed by contacting a T cell with a combination of PDL modified cell, anti-CD3 and anti-CD28 to induce Treg conversion. A converted T cell of the invention expresses Foxp3 and/or has the ability to suppress effector T cell activation. Assays for determining expression of Foxp3 and/or suppression of effector T cell activation are described elsewhere herein.

Accordingly, the present invention further comprises a method of multiplying, expanding or otherwise culturing a converted T cell that exhibits at least one regulatory T cell phenotype. The converted T cell of the invention can be expanded by about 10 fold, 100 fold, 1000 fold, 10,000 fold, 100,000 fold, 1,000,000 fold, 10,000,000 fold, or more using the methods disclosed herein. In one embodiment, the cells of the invention can be incubated in cell medium in a culture apparatus for a period of time or until the cells reach confluency before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The appropriate cell medium may be replaced during the culture of the cells at any time. Preferably, the cell medium is replaced about every 2 to 3 days. The desired cells are then harvested from the culture apparatus whereupon the cells can be used immediately or cryopreserved to be stored for use at a later time. The desired cells may be harvested by trypsinization, EDTA treatment, or any other procedure used to harvest cells from a culture apparatus.

The period of initial stimulation or restimulation as described herein (contact with agents as described herein) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The period of initial stimulation or restimulation as described further herein (contact with agents as described herein) can be longer, for example 1, 2, 3, 4, 5, 6, 7, 8, 9, 10, 11, 12, 13, 14, or more days. The cells of the invention can be re-stimulated for multiple rounds and yet retain natural Treg phenotype. For example, the cells of the invention can be re-stimulated for at least four rounds of restimulation.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but not limited to the seeding density, substrate, medium, and time between passaging.

The medium used to multiply the converted cells of the present invention comprises an agent that can stimulate CD3 and CD28 on the converted T cell. For example, an agent that can stimulate CD3 is an antibody to CD3, and an agent that can stimulate CD28 is an antibody to CD28. In one embodiment, the antibodies are conjugated or otherwise attached to a bead, such as a magnetic bead or a Dynal bead. Such beads are known in the art and are described elsewhere herein.

In another embodiment, the anti-CD3 and anti-CD28 antibodies are presented on an artificial presenting cell (aAPC). Accordingly, in certain aspects, the present invention includes expanding the converted cells of the invention in the presence of an aAPC. The extensive disclosure regarding aAPCs provided in WO 03/057171, US2003/0147869, US2006/0034810, 2004/0101519 are incorporated by reference as if set forth in their entirety herein.

Therapy to Inhibit Adverse Immune Responses Following Transplantation

The present invention includes a method of using converted Tregs as a therapy to inhibit graft versus host disease or graft rejection following transplantation. Accordingly, the present invention encompasses a method of contacting a donor transplant, for example a biocompatible lattice or a donor tissue, organ or cell, with a converted Treg prior, following, or simultaneously to transplantation of the transplant into a recipient. The converted Tregs serve to ameliorate, inhibit or reduce an adverse response by the donor transplant against the recipient.

As discussed elsewhere herein, the converted Tregs can be obtained from any source, for example, from the tissue donor, the transplant recipient or an otherwise unrelated source (a different individual or species altogether) for the use of eliminating or reducing an unwanted immune response by a transplant against a recipient of the transplant. Accordingly, converted Tregs can be autologous, allogeneic or xenogeneic to the tissue donor, the transplant recipient or an otherwise unrelated source.

In an embodiment of the present invention, the transplant is exposed to converted Tregs prior, at the same time, or after transplantation of the transplant into the recipient. In this situation, an immune response against the transplant caused by any alloreactive recipient cells would be suppressed by the converted Tregs present in the transplant. The converted Tregs are allogeneic to the recipient and may be derived from the donor or from a source other than the donor or recipient. In some cases, converted Tregs are autologous to the recipient and may be used to suppress an immune response against the transplant. In another case, the converted Tregs may be xenogeneic to the recipient, for example mouse or rat converted Tregs can be used to suppress an immune response in a human. However, it is preferable to use human converted Tregs in the present invention.

In another embodiment of the present invention, the donor transplant can be "preconditioned" or "pretreated" by treating the transplant prior to transplantation into the recipient in order to reduce the immunogenicity of the transplant against the recipient, thereby reducing and/or preventing graft versus host disease or graft rejection. The transplant can be contacted with cells or a tissue from the recipient prior to transplantation in order to activate T cells that may be associated with the transplant. Following the treatment of the transplant with cells or a tissue from the recipient, the cells or tissue may be removed from the transplant. The treated transplant is then further contacted with converted Tregs in order to reduce, inhibit or eliminate the activity of the T cells that were activated by the treatment of the cells or tissue from the recipient. Following this treatment of the transplant with converted Tregs, the converted Tregs may be removed from the transplant prior to transplantation into the recipient. However, some converted Tregs may adhere to the transplant, and therefore, may be introduced to the recipient with the transplant. In this situation, the converted Tregs introduced into the recipient can suppress an immune response against the recipient caused by any cell associated with the transplant. Without wishing to be bound to any particular theory, the treatment of the transplant with converted Tregs prior to transplantation of the transplant into the recipient serves to reduce, inhibit or eliminate the activity of the activated T cells, thereby preventing restimulation, or inducing hyporesponsiveness of the T cells to subsequent antigenic stimulation from a tissue and/or cells from the recipient. One skilled in the art would understand based upon the present disclosure, that preconditioning or pretreatment of the transplant prior to transplantation may reduce or eliminate the graft versus host response.

For example, in the context of umbilical cord blood, bone marrow or peripheral blood stem cell (hematopoietic stem cell) transplantation, attack of the host by the graft can be reduced, inhibited or eliminated by preconditioning the donor marrow by using the pretreatment methods disclosed herein in order to reduce the immunogenicity of the graft against the recipient. As described elsewhere herein, a donor hematopoietic stem and progenitor cell source can be pretreated with converted Tregs from any source, preferably with recipient converted Tregs in vitro prior to the transplantation of the donor marrow into the recipient. In a preferred embodiment, the donor marrow is first exposed to recipient tissue or cells and then treated with converted Tregs. Although not wishing to be bound to any particular theory, it is believed that the initial contact of the donor hematopoietic stem cell and progenitor cell source with recipient tissue or cells function to activate the T cells in the donor marrow. Treatment of the donor marrow with the converted Tregs induces hyporesponsiveness or prevents restimulation of T cells to subsequent antigenic stimulation, thereby reducing, inhibiting or eliminating an adverse effect induced by the donor marrow on the recipient.

In one embodiment of the present invention, a transplant recipient suffering from graft versus host disease or graft rejection may be treated by administering converted Tregs to the recipient to reduce, inhibit or eliminate the severity thereof from the graft versus host disease where the Tregs are administered in an amount effective to reduce or eliminate graft versus host disease.

In this embodiment of the invention, preferably, the recipient's converted Tregs may be obtained from the recipient prior to the transplantation and may be stored and/or expanded in culture to provide a reserve of converted Tregs in sufficient amounts for treating an ongoing graft versus host reaction. However, as discussed elsewhere herein, converted Tregs can be obtained from any source, for example, from the tissue donor, the transplant recipient or an otherwise unrelated source (a different individual or species altogether).

Therapy

The present invention further comprises a method for inhibiting proliferation of a T cell. Such inhibition can occur in vitro or in vivo, preferably in an animal, more preferably in a mammal, even more preferably in a human.

The method of the present invention comprises contacting a T cell with a converted Treg of the invention such that the proliferation of a T cell is inhibited by the converted Treg. The converted Treg cell can be administered using techniques well known in that art so that a converted Treg contacts, or is in proximity, to an immune cell, such as a T cell, dendritic cell, plasma cell, and the like.

Converted Tregs generated according to the methods of the present invention are uniform and potent suppressor cells. Further, the expanded converted Tregs of the present invention can be administered to an animal, preferably a mammal, even more preferably a human, to suppress an immune reaction, such as those common to autoimmune diseases such as diabetes, psoriasis, rheumatoid arthritis, multiple sclerosis, GVHD, enhancing allograft tolerance induction, transplant rejection, and the like. In addition, the cells of the present invention can be used for the treatment of any condition in which a diminished or otherwise inhibited immune response, especially a cell-mediated immune response, is desirable to treat or alleviate the disease.

The converted Tregs generated according to the present invention can also be used to treat autoimmune diseases. Examples of autoimmune disease include but are not limited to, Acquired Immunodeficiency Syndrome (AIDS, which is a viral disease with an autoimmune component), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenic purpura (ATP), Behcet's disease, cardiomyopathy, celiac sprue-dermatitis hepetiformis; chronic fatigue immune dysfunction syndrome (CMS), chronic inflammatory demyelinating polyneuropathy (CIPD), cicatricial pemphigold, cold agglutinin disease, crest syndrome, Crohn's disease, Degos' disease, dermatomyositis juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, pemacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjogren's syndrome, stiff-man syndrome, systemic lupus erythematosus, Takayasu arteritis, temporal arteritis/giant cell arteritis, ulcerative colitis, uveitis, vitiligo and Wegener's granulomatosis.

The converted Tregs generated according to the present invention can also be used to treat inflammatory disorders. Examples of inflammatory disorders include but are not limited to, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, sepsis, stroke, transplantation of tissue and organs, vasculitis, diabetic retinopathy and ventilator induced lung injury.

Cells of the invention can be administered in dosages and routes and at times to be determined in appropriate clinical trials. Cell compositions may be administered multiple times at dosages within these ranges. The cells of the invention may be combined with other methods. The cells of the invention for administration may be autologous, allogeniec or xenogenic to the patient undergoing therapy.

The administration of the cells of the invention may be carried out in any convenient manner. The cells of the present invention may be administered to a patient subcutaneously, intradermally, intramuscularly, by intravenous (i.v.) injection, or intraperitoneally. In some instances, the cells of the invention are administered to a patient by intradermal or subcutaneous injection. In other instances, the cells of the invention are administered by intravenous injection. In other instances, the cells of the invention are injected directly into a tumor or lymph node.

The cells of the invention can also be administered using any number of matrices. The present invention utilizes such matrices within the novel context of acting as an artificial lymphoid organ to support, maintain, or modulate the immune system, typically through modulation of T cells. Accordingly, the present invention can utilize those matrix compositions and formulations which have demonstrated utility in tissue engineering. Accordingly, the type of matrix that may be used in the compositions, devices and methods of the invention is virtually limitless and may include both biological and synthetic matrices. In one particular example, the compositions and devices set forth by U.S. Pat. Nos. 5,980,889; 5,913,998; 5,902,745; 5,843,069; 5,787,900; or 5,626,561 are utilized, as such these patents are incorporated herein by reference in their entirety. Matrices comprise features commonly associated with being biocompatible when administered to a mammalian host. Matrices may be formed from natural and/or synthetic materials. The matrices may be non-biodegradable in instances where it is desirable to leave permanent structures or removable structures in the body of an animal, such as an implant; or biodegradable. The matrices may take the form of sponges, implants, tubes, telfa pads, fibers, hollow fibers, lyophilized components, gels, powders, porous compositions, or nanoparticles. In addition, matrices can be designed to allow for sustained release of seeded cells or produced cytokine or other active agent. In certain embodiments, the matrix of the present invention is flexible and elastic, and may be described as a semisolid scaffold that is permeable to substances such as inorganic salts, aqueous fluids and dissolved gaseous agents including oxygen.

A matrix is used herein as an example of a biocompatible substance. However, the current invention is not limited to matrices and thus, wherever the term matrix or matrices appears these terms should be read to include devices and other substances which allow for cellular retention or cellular traversal, are biocompatible, and are capable of allowing traversal of macromolecules either directly through the substance such that the substance itself is a semi-permeable membrane or used in conjunction with a particular semi-permeable substance.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compositions of the present invention and practice the claimed methods. The following working examples therefore, specifically point out the preferred embodiments of the present invention, and are not to be construed as limiting in any way the remainder of the disclosure.

Example 1

PDL1 Directly Modulates Th1 Cell Differentiation

Immune surveillance by T helper type 1 (Th1) cells is critical for the host response to tumors and infection, but also contributes to autoimmunity and graft-versus-host disease (GvHD) after transplantation. The inhibitory molecule programmed death ligand-1 (PDL1) has been shown to anergize human Th1 cells, but other mechanisms of PDL1-mediated Th1 inhibition such as the conversion of Th1 cells to a regulatory phenotype have not been well characterized. The experiments disclosed herein were performed to determine whether PDL1 may cause Th1 cells to manifest differentiation plasticity.

The results presented herein demonstrate that conventional T cells or irradiated K562 myeloid tumor cells overexpressing PDL1 converted TBET$^+$ Th1 cells into FOXP3 regulatory T cells ($T_{REGS}$) in vivo, thereby preventing human-into-mouse xenogeneic GvHD (xGvHD). Either blocking PD1 expression on Th1 cells by siRNA targeting or abrogation of PD1 signaling by SHP1/2 pharmacologic inhibition stabilized Th1 cell differentiation during PDL1 challenge and restored the capacity of Th1 cells to mediate lethal xGVHD. PD1 signaling therefore induces human Th1 cells to manifest in vivo plasticity, resulting in a $T_{REG}$ phenotype that severely impairs cell-mediated immunity. Converting human Th1 cells to a regulatory phenotype with PD1 signaling provides a potential way to block GvHD after transplantation. Moreover, because this conversion can be prevented by blocking PD1 expression or pharmacologically inhibiting SHP1/2, this pathway provides a new therapeutic direction for enhancing T cell immunity to cancer and infection.

The materials and methods employed in these experiments are now described.

Materials and Methods

Mice

Various immune-deficient murine hosts were used, depending upon availability. Female RAG2$^{-/-}$cγ$^{-/-}$ mice were obtained from Taconic and used at 8-12 weeks of age. Experiments were performed according to a protocol approved by the NCI Animal Care and Use Committee. Mice were housed in a sterile facility and received sterile water and pellets. Mice were injected with 0.1 ml clodronate containing liposomes (Encapsula Nanoscience) for macrophage depletion and given low-dose irradiation (350 cGy). Female NOD/SCID mice were obtained from Jackson Laboratory and conditioned with low dose radiation (450 cGy). NODLtSz-scidIL2Rγ$^{null}$ mice (NSG) were obtained from Jackson Laboratory; NSG hosts did not undergo conditioning prior to human cell transfer.

Antibodies and Reagents

X-VIVO 20 media was obtained from BioWhitaker and AB serum was from Gem Cell. CD4 microbeads were from Miltenyi Biotec. Anti-CD3, anti-CD28 and PDL1-Fc chimera coated tosyl-activated magnetic beads were manufactured. Rapamycin was from Wyeth (Rapamune®). Recombinant human (rh) IL-2 was from PeproTech and rhIFN-α-2b was from Schering Plough. Recombinant PDL1-Fc chimera was from R&D systems. All other antibodies (unless otherwise stated) were provided by BD Biosciences; anti-human FOXP3 PE was from Biolegend. Luminex kits for detection of IFN-γ and TNF-α were from Bio-Rad (Hercules, Calif.). 5-(and -6)-carboxyfluorescein diacetate, succinimidyl ester [5(6)-CFDA, SE; CFSE] was from Invitrogen. Zidovudine (AZT) was from Glaxosmithkline.

Vector Design and Construction pDY.cPPT.EF-1α.EGFP.WPRE.SIN was modified from pHR'.cPPT.EF-1α.EGFP.WPRE.SIN by deletion of non-essential elements of the original transfer vector backbone and LTR sequences. Human codon-optimized, human PD-L1 cDNA was synthesized by Genscript and subcloned into pDY.cPPT.EF-1α.CD19ΔTMPK.WPRE.SIN (control-LV) to yield pDY.cPPT.EF-1α.CD19ΔTMPK.IRES.PDL1.WPRE.SIN (PDL1-LV).

Fidelity of all vectors was validated by bidirectional sequencing. LVs pseudotyped with vesicular stomatitis virus-glycoprotein (VSV-g) were generated as described previously (Yoshimitsu, et al., 2004, Proc Natl Acad Sci USA 101:16909-16914). In addition, we incorporated a fourth plasmid, pAdVAntage™ vector from Promega to increase LV titers. Virus supernatants were harvested 48 hours and 72 hours after transfection, filtered using 0.45-μm filter, and concentrated at 50,000×g for 2 hours using an Optima L-100 XP Ultracentrifuge. LV pellets were re-suspended in serum-free X-VIVO 20 media. Typical functional titers of concentrated LVs were in the range of $5\times10^8$ to $1\times10^9$ IU/mL.

Human T Cell Transduction with Lentivirus

Normal donor peripheral blood cells were collected by apheresis on an IRB-approved protocol. Total lymphocytes were isolated by elutriation (Abrahamsen, et al., 1991, J Clin Apher 6:48-53). Total $CD4^+$ T cells were then enriched by CD4 microbeads according to manufacturer instructions. $CD4^+$ T cells were co-stimulated at a 3 bead:1 T cell ratio in media containing IL-2 (20 IU/ml) and rapamycin (1 μM). At day 3 of culture, cells were washed and replaced at a concentration of $2\times10^5$ cells/ml in media containing IL-2 and lentiviral supernatant at an MOI of 20.

Flow Cytometry

T cells were washed with PBS supplemented with 0.1% BSA and 0.01% azide, and stained using anti-: CD4 APC (clone: RPA-T4), CD19 PE (clone: H1B19), and PDL1 FITC (clone: M1H1). For assessment of cell death, T cells were stained for surface markers (CD4 FITC, CD19 PE and PDL1 PE-cy7), resuspended in Annexin V buffer, and stained with AV APC and 7AAD according to manufacturer's instructions. For in vivo monitoring of human T cells, splenocytes were stained with CD45 FITC (clone: H130), CD3 Pecy5 (clone: H1T3a), PDL1 Pe-cy7, PD1 APC (clone: M1H4), CD80 PE (clone: L307.4), and CD19 APC-cy7 (clone: SJ25C1). For intra-cellular (IC) flow cytometry, fixation and permeabilization buffer was utilized (eBioscience). IC flow cytometry was performed with combinations of CD45 FITC, CD3 Pecy5, PDL1 Pecy7, TBET APC (clone: 4B10; eBioscience), FOXP3 PB (clone 249D; eBioscience), and CD19 APC-cy7; other reagents for IC flow cytometry included IL-2 FTTC (clone: MQ1-17H12), IFN-γ PE (clone: 45.133), CD3 Pecy5, PDL1 Pecy7, TNF-α APC (clone: MAB11; eBioscience), FOXP3 PB, CD45 APC-cy7 or CD45 FITC, active Caspase-3 PE, CD3 Pecy5, PDL1 Pecy7, PD1 APC, FOXP3 PB, and CD19 APC-cy7.

STAT Phosphorylation Assays

Flow cytometry to assess phosphorylation status of STAT molecules was performed using BD phosphoflow kit containing BD lyse/fix buffer and perm buffer III; STAT1 A488 (clone 4a) and STAT3 A647 (clone49; p-stat3) antibodies were utilized. Briefly, cells were incubated for 15 min with IFN-γ, fixed for 15 min at 37° C. with phospho-lyse buffer, and then fixed in perm buffer III (30 min, 4°). Cells were washed with FACS buffer and stained for STAT and surface markers, incubated at room temperature (20 min), and analyzed with FACSCalibur® and CellQuest® software (BD). Nuclear lysates of stimulated T cells were tested for activated nuclear STAT1 and STAT3 by using the TransAM DNA binding ELISA assay obtained from Active Motif.

Protein Determination by Western Blot Analysis

Protein lysates were obtained from T cell cultures that were subjected to siRNA transduction. Lysates were run on 10-20% SDS-PAGE gels and transferred onto nitrocellulose membrane. Membranes were blocked with 5% milk in TBST buffer (20 mmol/L Tris HCl, 500 mmol/L NaCl, and 0.01% Tweeen 20) and incubated overnight at 4° C. with primary antibodies (Ab) in TBST containing either 5% milk or BSA. Immunoreactivity was detected by sequential incubation with HRP-conjugated secondary Ab and enzymatic chemiluminescence (Cell Signaling Technology). Primary Abs used were from Cell Signaling and included anti-: SHP1, SHP2, Smad2, pSmad2, and beta-actin.

siRNA Knockdown of PD1 and SHP1/2 siRNA oligonucleotides for PD1 (P1, P2, P3, and P4), SHP1, SHP2 and AllStar Negative control siRNA were purchased from Qiagen (Valencia, Calif.). Transfection of siRNA was performed according to manufacturer's instructions (Amaxa). Transfected cells were co-stimulated as previously described and harvested for real time PCR, protein, and functional assays at day 3 post-transfection. PD1 knockdown was measured by flow cytometry and SHP1/2 knockdown was measured by western blotting. All in vivo experiments were performed with P4 siRNA, which had the most efficient PD1 knockdown. The cells were further flow sorted for >99% purity of $PD1^{kd}$ population and then adoptively transferred into mice.

K562 Cell Culture

Representative K562 cell can be obtained from the American Type Culture Collection (ATCC, Manassas, Va.; catalog #CCL-243). Briefly, cells were grown in suspension in IMDM medium supplemented with 10% characterized fetal bovine serum (Invitrogen, Carlsbad, Calif.), 100 units/mL penicillin G, 100 g/ml streptomycin, and 0.29 mg/mL L-glutamine (Invitrogen, Carlsbad, Calif.) at 37°, 5% $CO_2$, and 95% humidity. Cells were allowed to expand until reaching saturation at which point they were subcultured or harvested for assay use.

Xenogeneic GVHD Model

Human effector $CD4^+Th1$ (Th1) cells were generated by T cell culture for 6 days with co-stimulation and expansion in rhIL2 (20 IU/ml), anti-IL-4 (100 ng/ml), rhIFN-α-2b ($1\times10^6$ IU/ml), and rapamycin (1 μM) (Amarnath, et al., 2010, Autophagy 6: 4). On day 6 of culture, Th1 cells were harvested and injected i.v. by retro-orbital injection (Nervi, et al., 2007, Exp Hematol 35:1823-1838) into immune-deficient murine hosts; Th1 cell dose was $1\times10^6$ cells/recipient. Specific cohorts additionally received ex vivo generated $T_{REG}$ cells (generated from $CD4^+CD127^-$ cells; dose of $0.5\times10^4$ cells/recipient); other cohorts received non-polarized $CD4^+$ T cells transduced with control-LV or PDL1-LV (dose of $0.5\times10^4$ or $1\times10^6$ cells/recipient, as indicated in figure legend). Mice were challenged with LPS at day 5 post-transplant as indicated. In vivo experiments were also performed where Th1 cells were generated ex vivo using flow sorted $CD4^+CD127^+CD25^-CD45RA^+$ T cells as the culture input population and using a longer, 12-day Th1 cell expansion and polarization interval. In the natural history model of x-GVHD, LPS challenge was not performed; additional in vivo experiments were performed using human Th1 cells harvested at day 50 post-transplant of the natural history x-GVHD model. AZT was administered by i.p. injection (twice per day; dose of 50 mg/kg/day). The myeloid tumor cell line K562 (unmodified or PDL1 transduced) were used after irradiation (10,000 rads).

DNA Methylation Analysis

Th1 cells were either co-cultured for 3 days with PDL1-coated beads or isolated post-BMT from PDL1-treated or untreated mice. Genomic DNA was harvested and quantification of the degree of methylation at the FOXP3-TSDR locus was detected by real time PCR method (performed by Epiontis).

Statistical Analysis

Flow cytometry and cytokine data were analyzed using student's 2-tailed t tests. Comparison values of $p \leq 0.05$ were considered statistically significant. LPS lethality data was analyzed using log rank test.

The results of the experiments are now described.

Figures 8A, 8B:
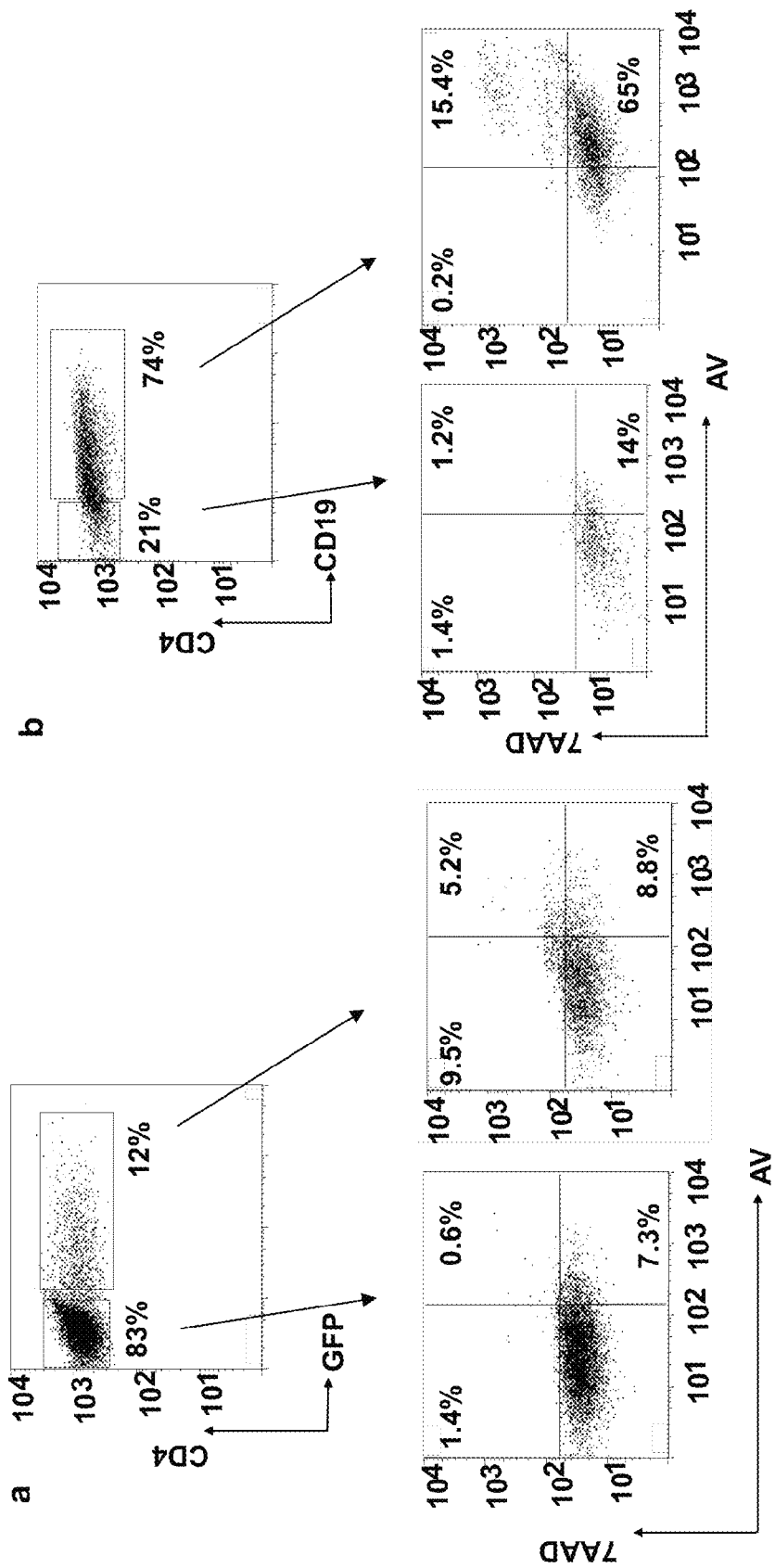
FIGS. 8A through 8D, is a series of images demonstrating that TMPK cell fate safety switch is functional in vitro and in vivo. Human primary T cells were transduced with PDL1-LV or control eGFP-LV; PDL1-LV cells were then enriched by flow sorting. Transduced T cells were treated ex vivo with AZT (100 μM; three days) and cell death was measured (Annexin V, 7AAD).
Figures 9A, 9B, 9C:
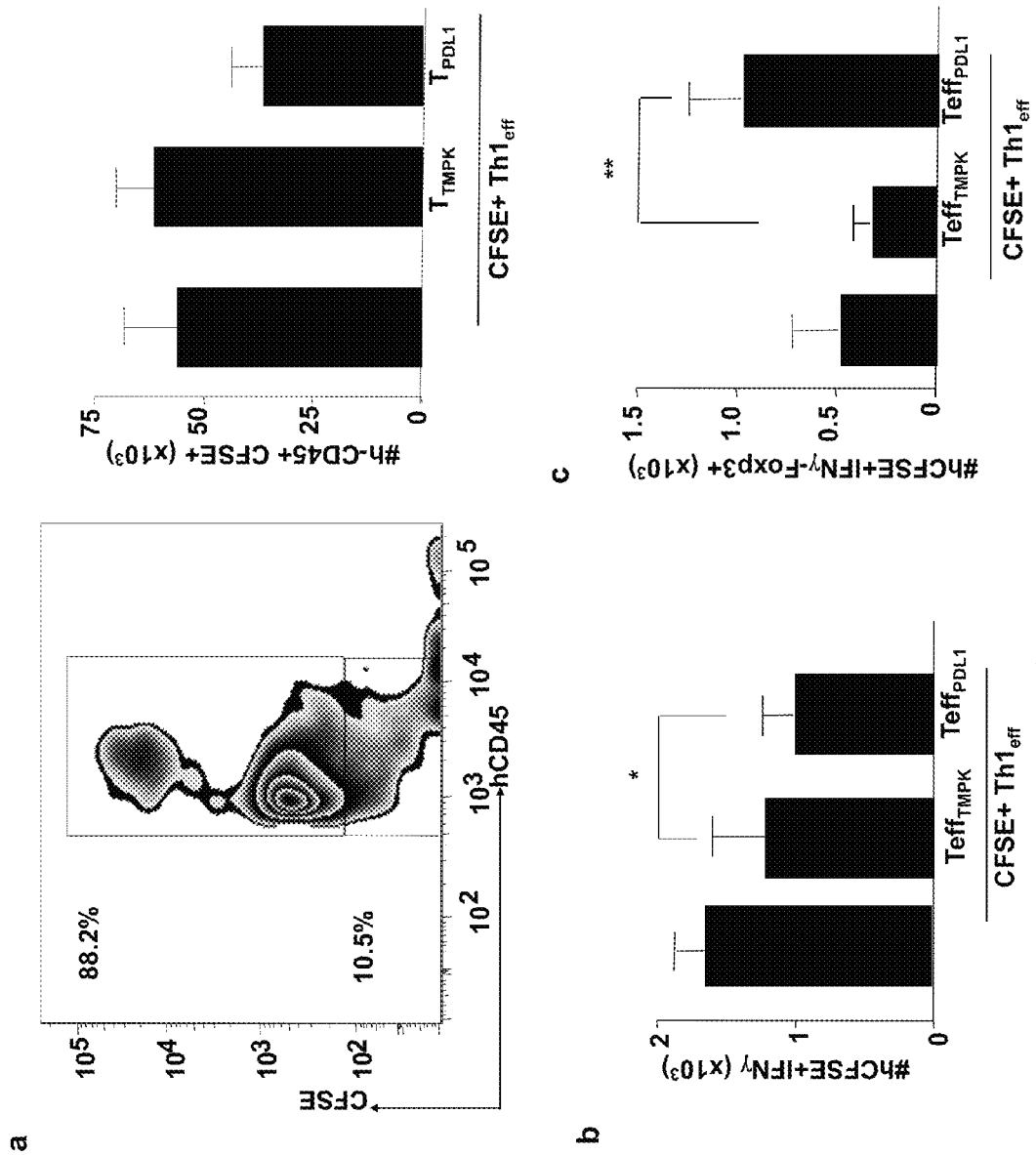
FIGS. 9A through 9C, is a series of images demonstrating that PDL1-expressing effector T Cells alter the balance of Th1 and Treg cells in vivo. Human Th1 cells were CFSE-labeled and adoptively transferred either alone or with control-LV or PDL1-LV transduced T cells.

Th1-Mediated Xenogeneic GVHD is Abrogated by $T_{REG}$ Cells or PDL1-Expressing T Cells To directly evaluate the effect of PDL1 on Th1 cell biology, a lentivirus (LV) was constructed to incorporate the full-length PDL1 cDNA. The vector, which encoded a fusion protein of TMPK for cell fate control (Sato, et al., 2007, Mol Ther 15:962-970) and CD19 for cell surface marking, is referred to as "CD19.TMPK/PDL1-LV" (FIG. 8A depicts the vector design). Transduction of purified human CD4+ T cells with a control-LV that expressed the fusion protein alone (CD19.TMPK-LV) or with CD19.TMPK/PDL1-LV yielded nearly 30% productive infection frequency by CD19/PDL1 flow cytometry analyses (FIG. 8B left panels [representative data] and right panels [summary of n=7]). The functionalities of the TMPK cell fate control sequence was confirmed in vitro and in vivo by measuring the sensitivity of LV transduced T cells to AZT addition (FIG. 9).

Figures 1D, 1E:
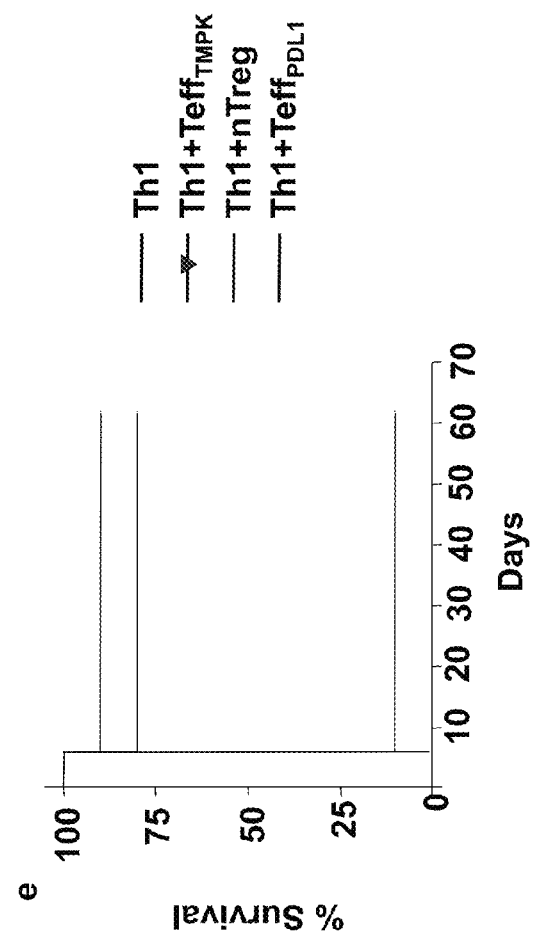
Figures 8C, 8D:
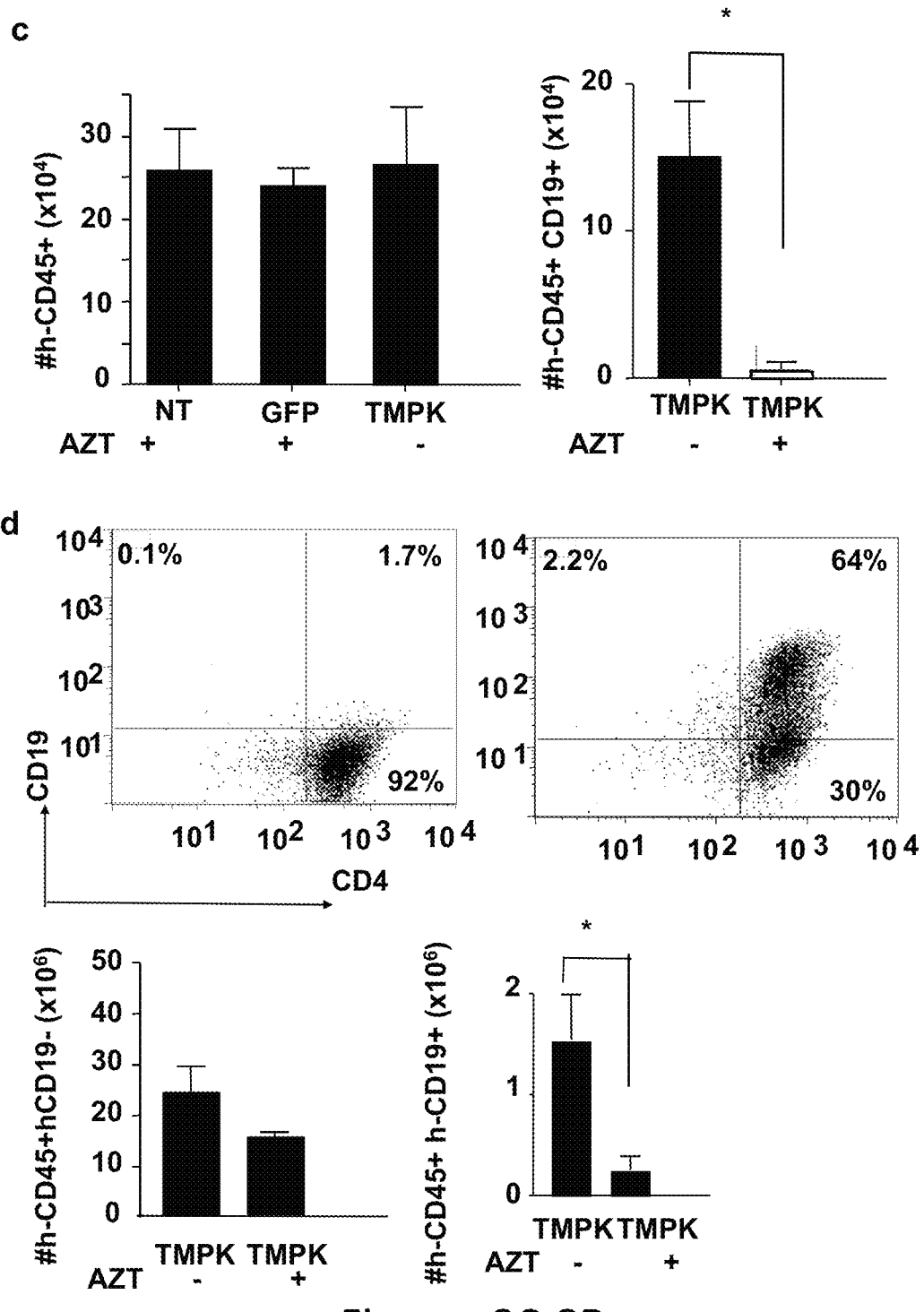

The next experiment was performed to compare T cells transduced with CD19.TMPK-LV (Teff$_{PDL1}$) against purified $T_{REG}$ cells for their capacity to prevent Th1 cell-mediated xGVHD. Th1-polarized human T cells (Th1) were adoptively transferred alone or with either control LV-transduced T cells (Teff$_{TMPK}$), PDL1 LV-transduced T cells (Teff$_{PDL1}$), or purified $T_{REGS}$. Hosts were subsequently challenged with LPS to induce cytokine-mediated xGVHD (Amarnath, et al., 2010, Autophagy 6: 4). $T_{REG}$ cells and PDL1 LV-transduced T cells similarly inhibited post-transplant T cell IFN-γ production (FIGS. 1A and 1B), systemic TNF-α production (FIG. 1C), and lethality (FIG. 1D)). Recipients of Th1 cells in combination with Teff$_{PDL1}$ cells or purified $T_{REG}$ cells were protected long-term from xGVHD through 65 days post-transplant (FIG. 1E). In vivo PDL1 expression on Teff$_{PDL1}$ cells was stable in these long-term survivors (FIGS. 8C, 8D and 8E). Therefore, forced expression of PDL1 on conventional T cells mimicked $T_{REG}$ therapy for inhibition of Th1 cell-mediated xGVHD.

Human Th1 Cells Show Rapid Plasticity In Vivo to a $T_{REG}$ Phenotype Via PDL1

Figures 10A, 10B, 10C:
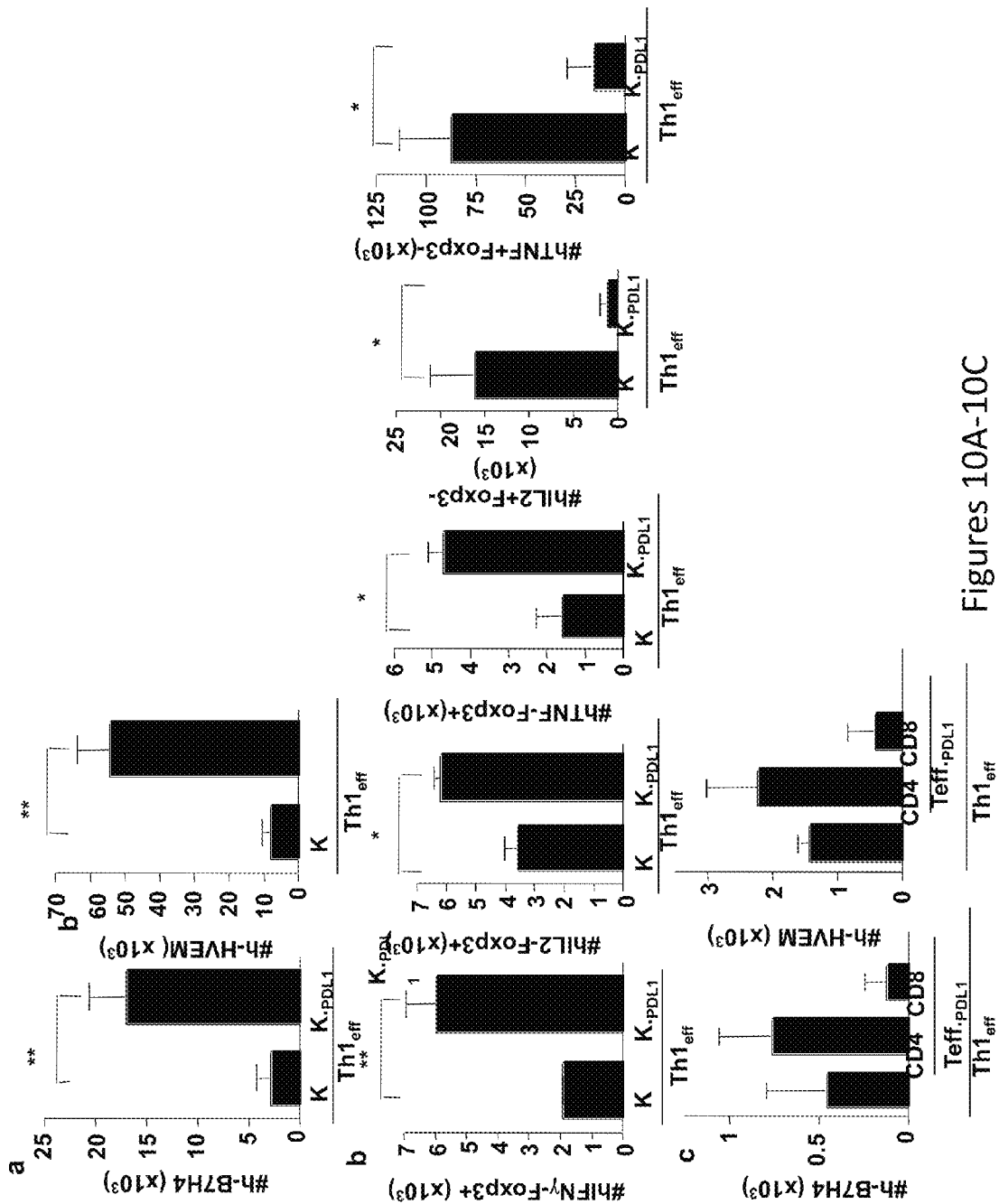
FIGS. 10A through 10F, is a series of images demonstrating that Th1 cells expanded from naïve human CD4+ T cells and human pathogenic Th1 cells are responsive to PDL1-mediated conversion. Polarized Th1 cells were adoptively transferred into NSG mice along with irradiated K562 cells (K) or K562 cells expressing PDL1 (K.PDL1).
Figures 10D, 10E, 10F:
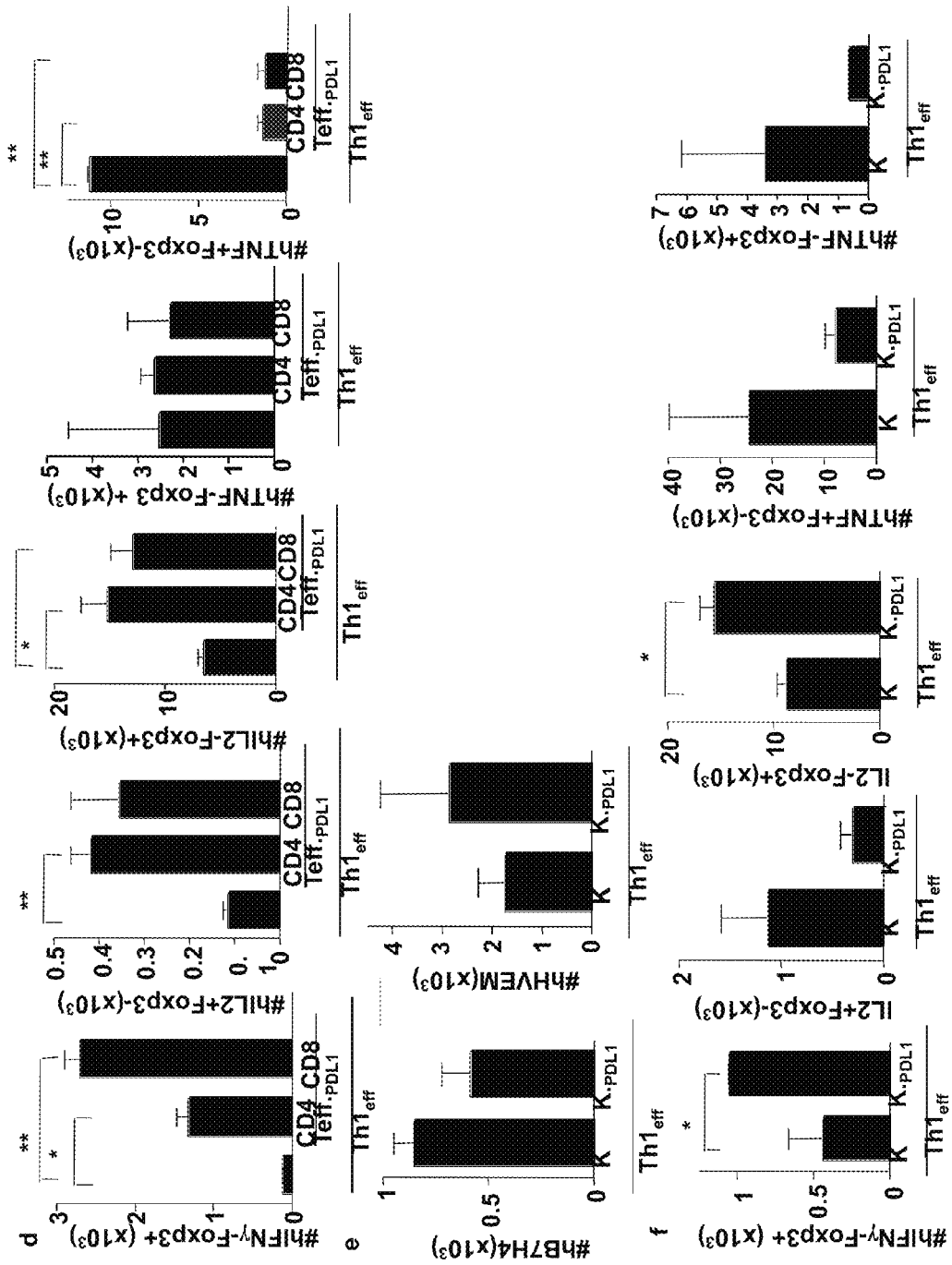

To confirm that PDL1 induced Th1 cell differentiation plasticity rather than clonal deletion, the fate of CFSE-labeled Th1 cells was monitored at 24 hour after transplant (representative flow data; FIG. 10A, left panel). PDL1 LV-transduced T cells did not abrogate Th1 cell engraftment (FIG. 10A, right panel), thereby ruling out a clonal deletion mechanism. PDL1 LV-transduced T cells down-regulated Th1 cell IFN-γ production (FIG. 10B) and increased the absolute number of Th1 cells that expressed FOXP3 but did not secrete IFN-γ (FIG. 10C). As such, Th1 cells showed differentiation flexibility towards a regulatory phenotype through interactions with PDL1.

Figures 2A, 2B, 2C, 2D, 2E:
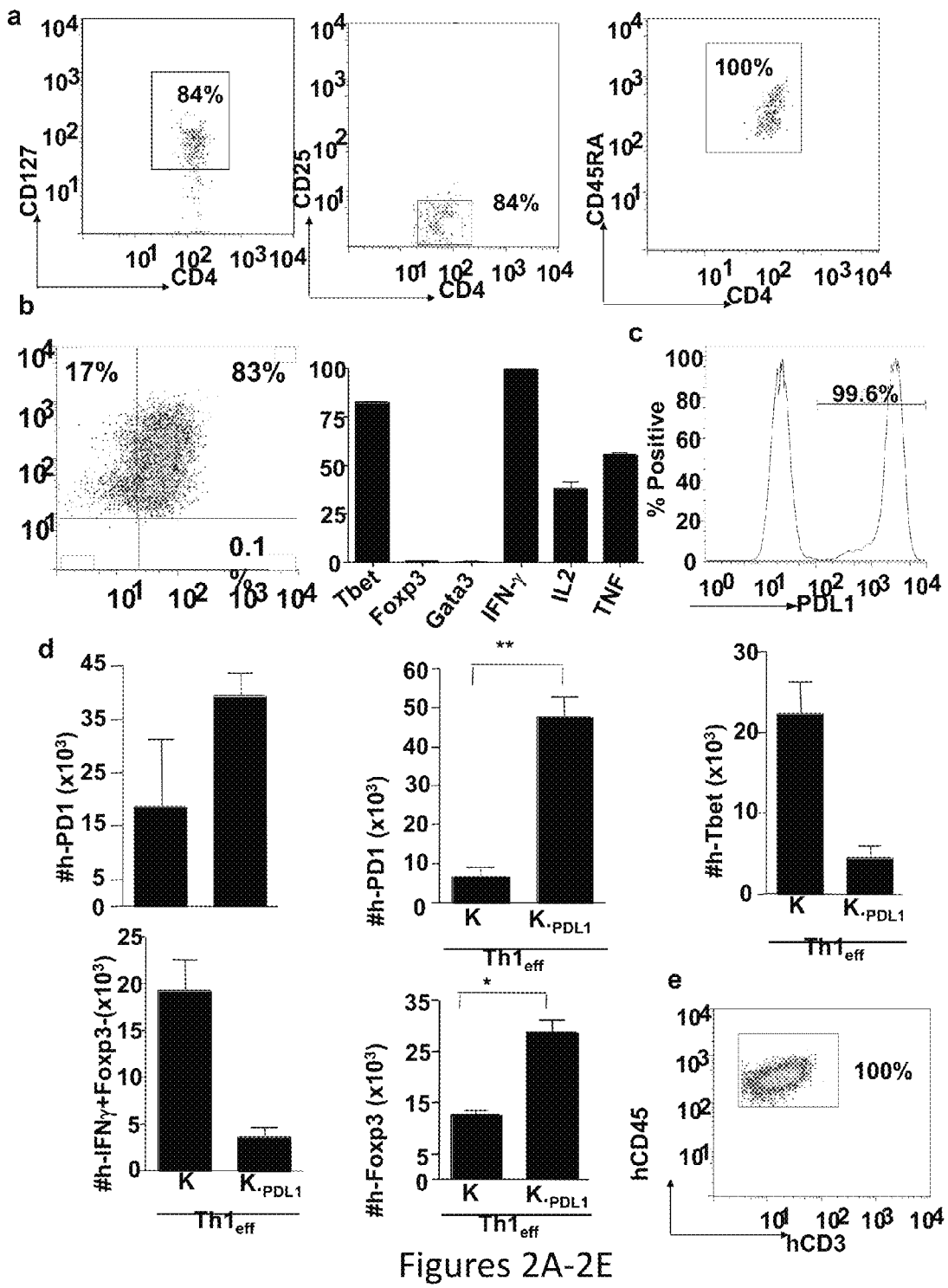
FIG. 2A is an image demonstrating that naïve CD4$^+$ T cells were purified by flow sorting based on their CD127$^+$, CD25$^-$, and CD45RA$^+$ status. Sorted populations were expanded for 12 days in the presence of anti-CD3, anti-CD28 coated beads in media containing IL-2, an antibody to IL4, and rhIL12.
FIG. 2B is an image demonstrating that at day 12, Th1 cells were harvested and restimulated with PMA and ionomycin and subjected to intra-cellular flow cytometry. The right panel of FIG. 2B depicts a representative flow plot showing percentage of Th1 cells that were IFN-γ$^+$TBET$^+$. The left panel of FIG. 2B is an image depicting the characterization of Th1 cells based on transcription factor profile and cytokine secretion.
FIG. 2C is an image depicting a representative histogram of PDL1 expression on the transduced K562 tumor cell line; control K562 cell line.
FIG. 2D is an image demonstrating that expanded Th1 cells were adoptively transferred into NSG mice alone or in combination with K562 cells alone (K) or K562 cells that expressed PDL1 ($K_{PDL1}$). At day 5 after adoptive transfer, splenocytes were harvested and absolute numbers of cells that expressed hPD1, hCD80, hTBET, hFOXP3 and hIFN-γ were quantified.
FIG. 2E is an image demonstrating that human Th1 cells were adoptively transferred into NSG mice and flow cytometry was performed at day 50 after transplant to detect human Th1 cell engraftment.
Figures 11A, 11B, 11C:
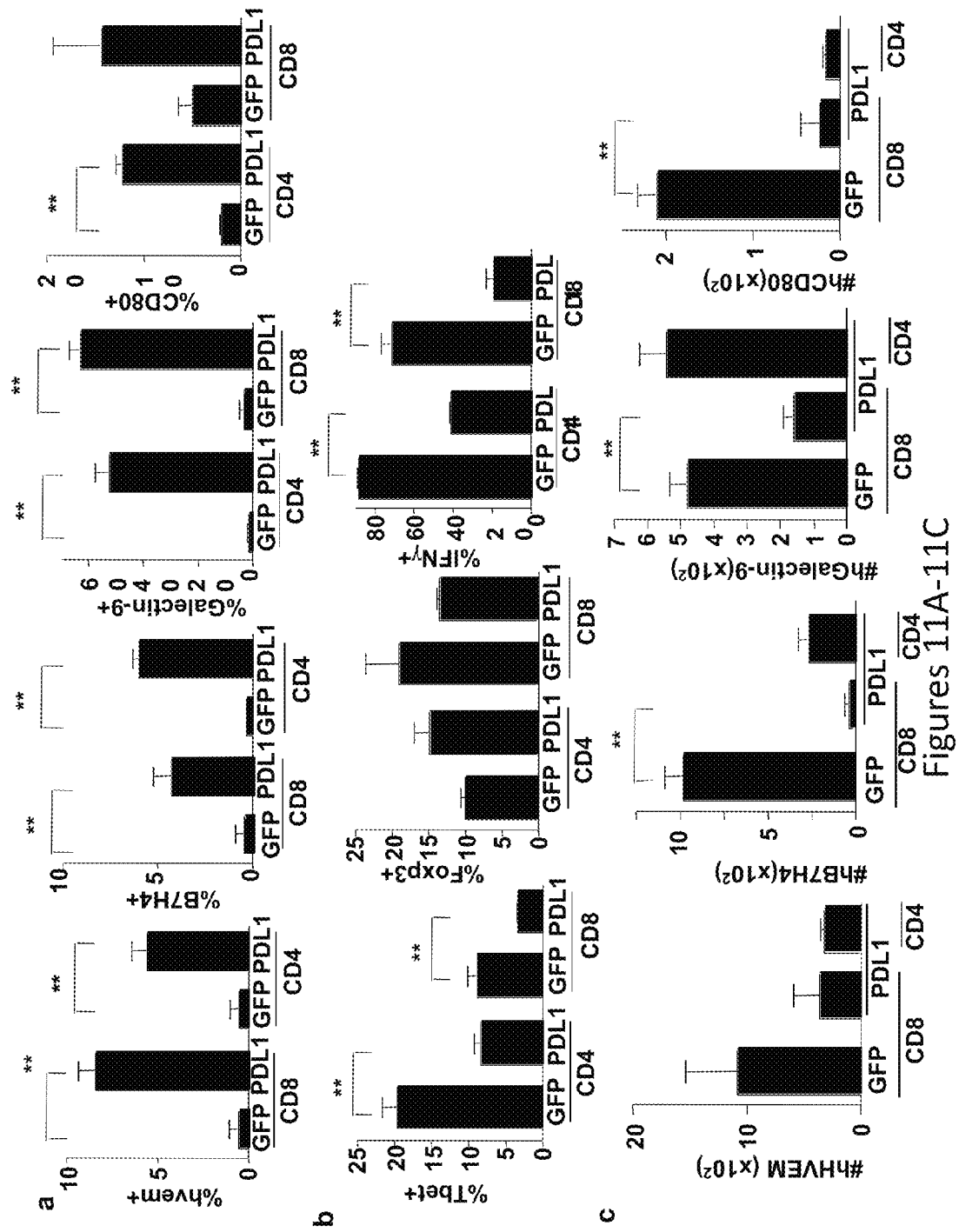
FIG. 11A is an image demonstrating that stably transduced T cells were then characterized for the expression of coinhibitory molecules such as HVEM, B7H4, galectin-9 and CD80.
FIG. 11B is an image demonstrating that transfected T cells were then stimulated with PMA and ionomycin for 4 hrs following which they were characterized for transcription factors TBET, FOXP3 and IFN-γ expression.
FIG. 11C is an image demonstrating that human transduced T cells were co-injected along with Th1 cells into immunocompromised murine hosts. Splenocytes were harvested at day 5 and LV transduced cells were characterized by gating on CD45+GFP+ or CD45+CD8+PDL1+ or CD45+CD4+PDL1+ populations. Absolute numbers of HVEM, B7H4, galectin 9 and CD80 are shown.

PDL1-Mediated Plasticity Occurs in Ex Vivo Generated Purified Th1 Cells and In Vivo-Derived Pathogenic Th1 Cells Highly purified human Th1 cells were generated ex vivo using flow sorting to enrich for naïve CD4+ T cells at culture initiation (FIG. 2A) and expansion under Th1 polarizing conditions for an extended, 12-day culture interval (FIG. 2B). Such highly polarized Th1 cells were injected in vivo along with irradiated K562 cells that were transduced with PDL1 (K562$_{PDL1}$) (FIG. 2C). Post adoptive transfer, K562$_{PDL1}$ treated human Th1 cells had increased expression of the PDL1 binding partners PD1 and CD80 (FIG. 2D, left panels), B7H4 and HVEM FIG. 11A), with a concomitant reduction in TBET, IFN-γ (FIG. 2D, middle panels) IL2 and TNFα (FIG. 11, right panels). Deviation from the Th1 phenotype correlated with an increase in FOXP3 expression (FIG. 2D, right panel; FIG. 11B, middle and left panels).

Figures 2F, 2G, 2H, 2I:
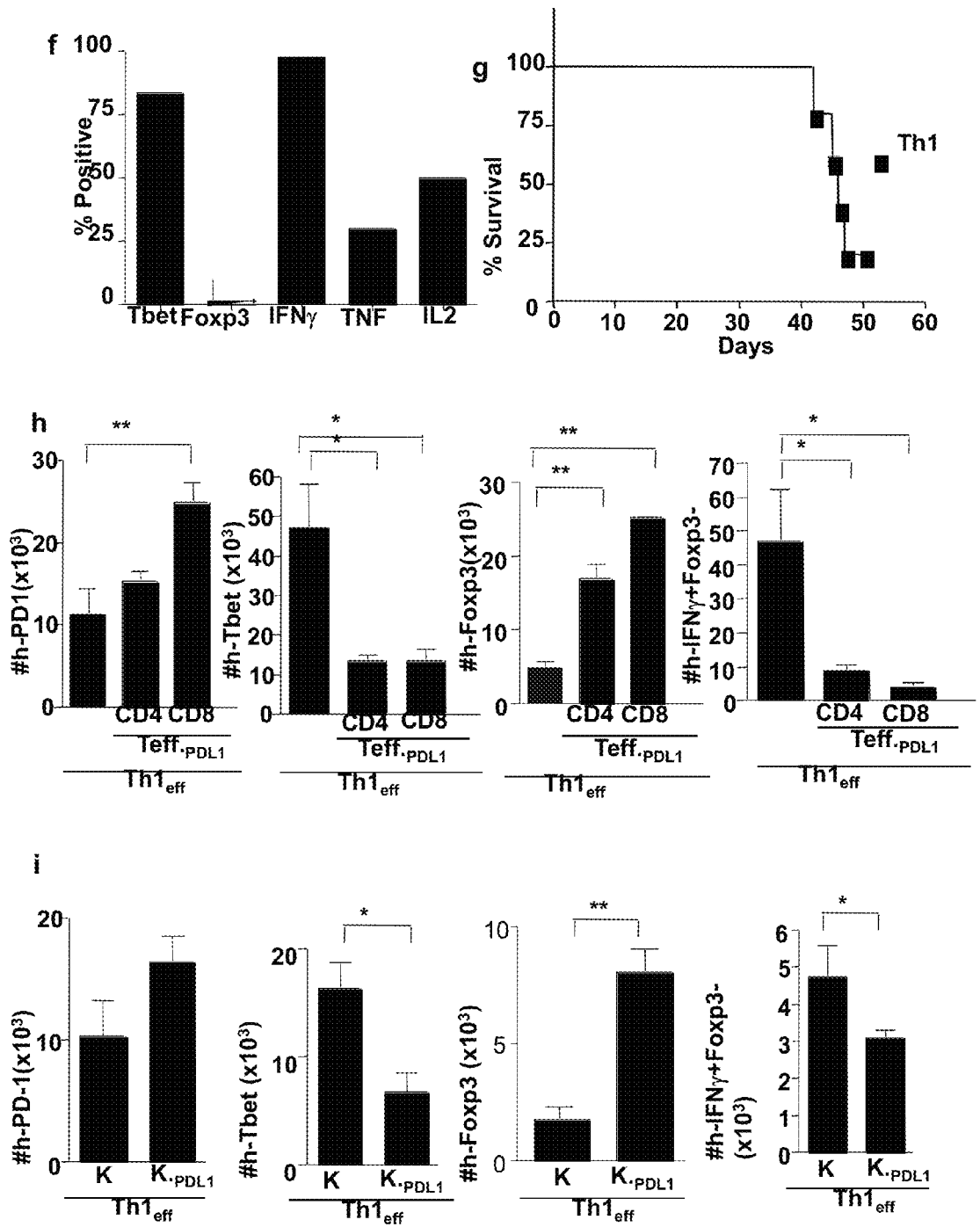
FIG. 2F is an image demonstrating that engrafted human Th1 cells were restimulated ex vivo and characterized for transcription factor and cytokine expression.
FIG. 2G is an image depicting a survival curve for human Th1 cell transfer into NSG hosts.
FIG. 2H is an image demonstrating that the in vivo-derived, pathogenic human Th1 cells were harvested at day 50 after transplant and transferred to secondary murine recipients either alone or in the presence of CD4$^-$ T cells expressing PDL1 or CD8$^+$ T cells expressing PDL1. At day 5 after adoptive transfer, splenocytes were harvested and absolute numbers of cells expressing hPD1, hTBET, hFOXP3 and hIFN-γ were quantified by flow cytometry.
FIG. 2I is an image demonstrating that additional experiments were performed where in vivo-derived pathogenic human Th1 cells were co-injected with irradiated K562 cells (K) or irradiated K562 cells expressing PDL1 ($K_{PDL1}$). Splenocytes were harvested at day 5 and absolute numbers of cells expressing hPD1, hTBET, hFOXP3 and hIFN-γ were quantified (* indicates p≤0.05, ** indicates p≤0.005).
Figures 11D, 11E, 11F:
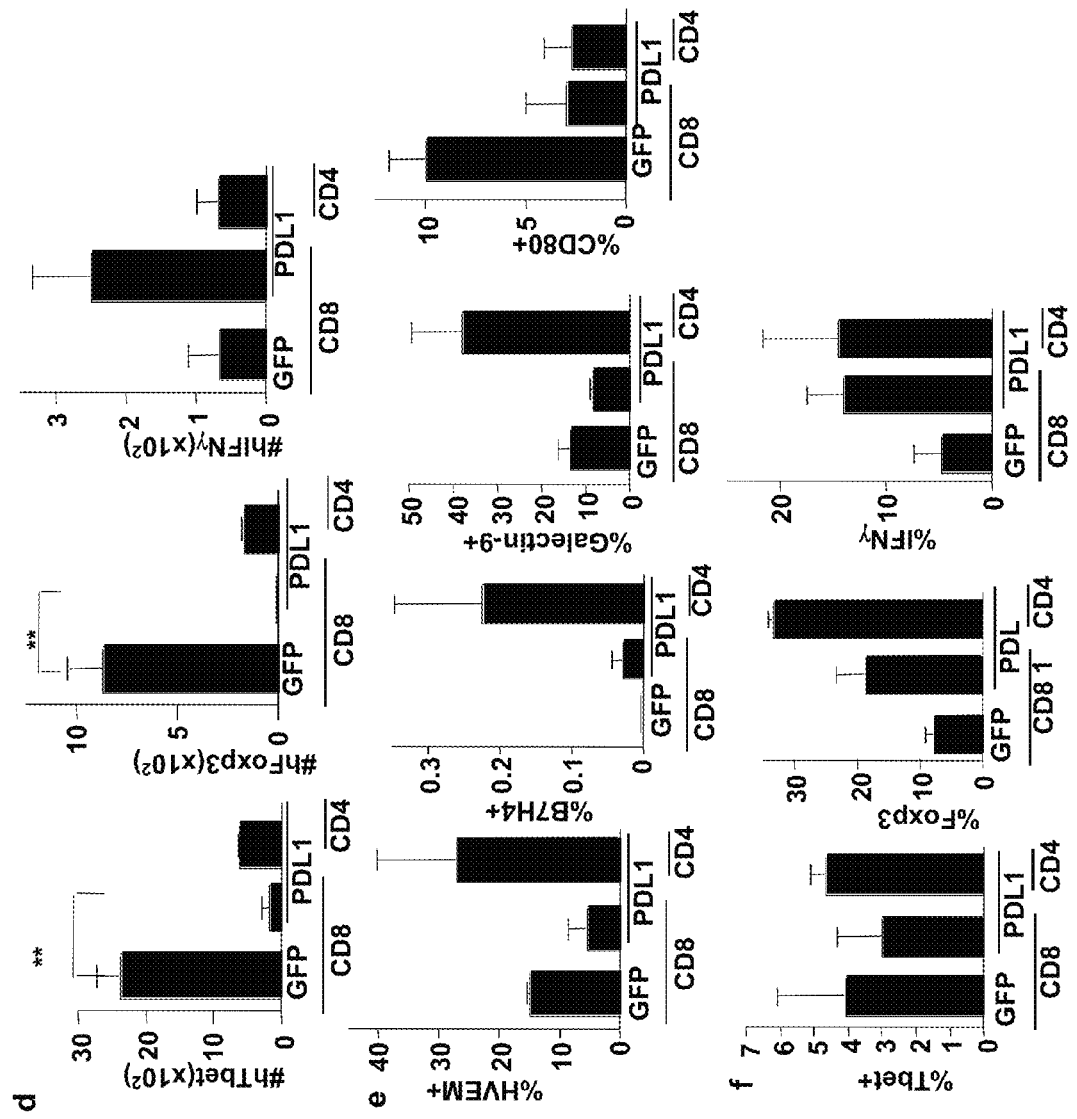
FIG. 11D is an image demonstrating that splenocytes were stimulated ex vivo and absolute numbers transduced human T cells expressing TBET, FOXP3 and IFN-γ were quantified.
FIG. 11E is an image demonstrating that in vitro experiments were set up where transduced CD8+ T cells and CD4+ T cells were co-cultured with CFSE+ Th1 cells for 3 days. On day 3 post transfer, transduced cells were gated as the CFSE-population and characterized for the expression of HVEM, B7H4, galectin 9 and CD80.
FIG. 11F is an image demonstrating that intracellular flow cytometry was performed to further characterize TBET, FOXP3 and IFN-γ expression of the transduced cells post co-culture (* indicates p≤0.05, ** indicates p≤0.005).

Experiments were designed to further assess the effect of PDL1 on human Th1 cells that were observed to be pathogenic in vivo on the basis of their causation of xenogeneic GVHD. Such pathogenic human Th1 cells (FIG. 2E) caused lethality in a subset of murine hosts (FIG. 2G) and upon T cell harvest at day 50 after transplant for secondary transfer experiments, were found to express an effector phenotype (FIG. 2F). Similar to in vitro polarized Th1 cells, in vivo-derived human Th1 cells with demonstrable pathogenicity were susceptible to PDL1-mediated plasticity. Such in vivo-derived human Th1 cells were similarly converted to a regulatory phenotype whether the PDL1 was delivered by CD4+ T cells or CD8+ T cells as PDL1 vehicle (FIG. 2H, FIGS. 11C and 11D); furthermore, PDL1-expressing K562 cells also converted the in vivo-derived human Th1 cells (FIG. 2I, FIGS. 11E and 11F).

Figures 12A, 12B:
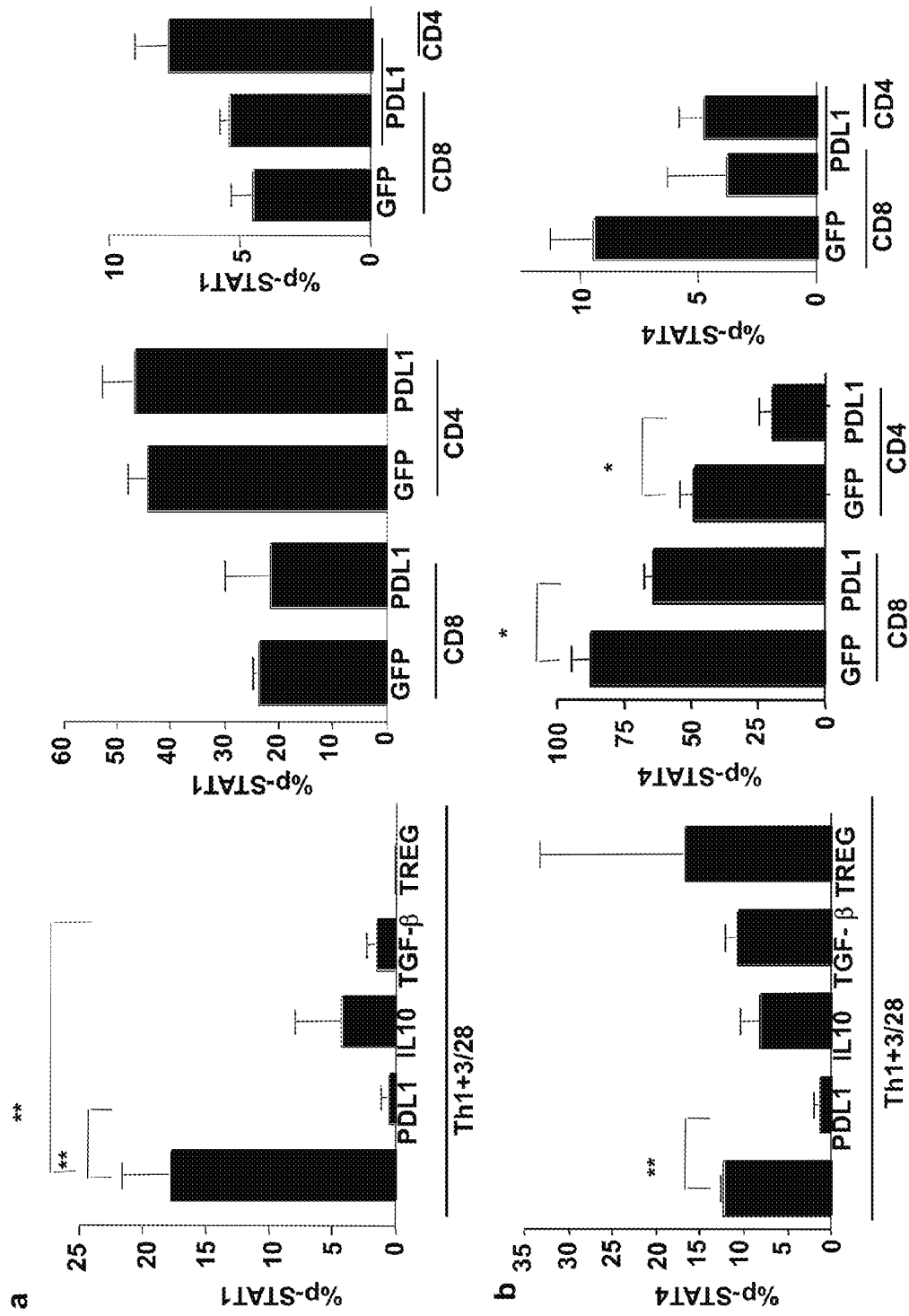
FIGS. 12A through 12E, is a series of images demonstrating that Th1 cells co-cultured with PDL1, IL10, TGF-β or TREG exhibit decreased effector activity independent of PD1 upregulation or FOXP3 expression. Human Th1 cells were labeled with CFSE and then co-cultured with either PDL1 beads, rhIL10 (100 ng/ml), rhTGF-β (2 ng/ml) or TREG cells (1:1; TREG:Th1 ratio) for 3 days. In some cultures, transduced CD4 or CD8 T cells expressing PDL1 was added to the co-culture.
Figures 12C, 12D, 12E:
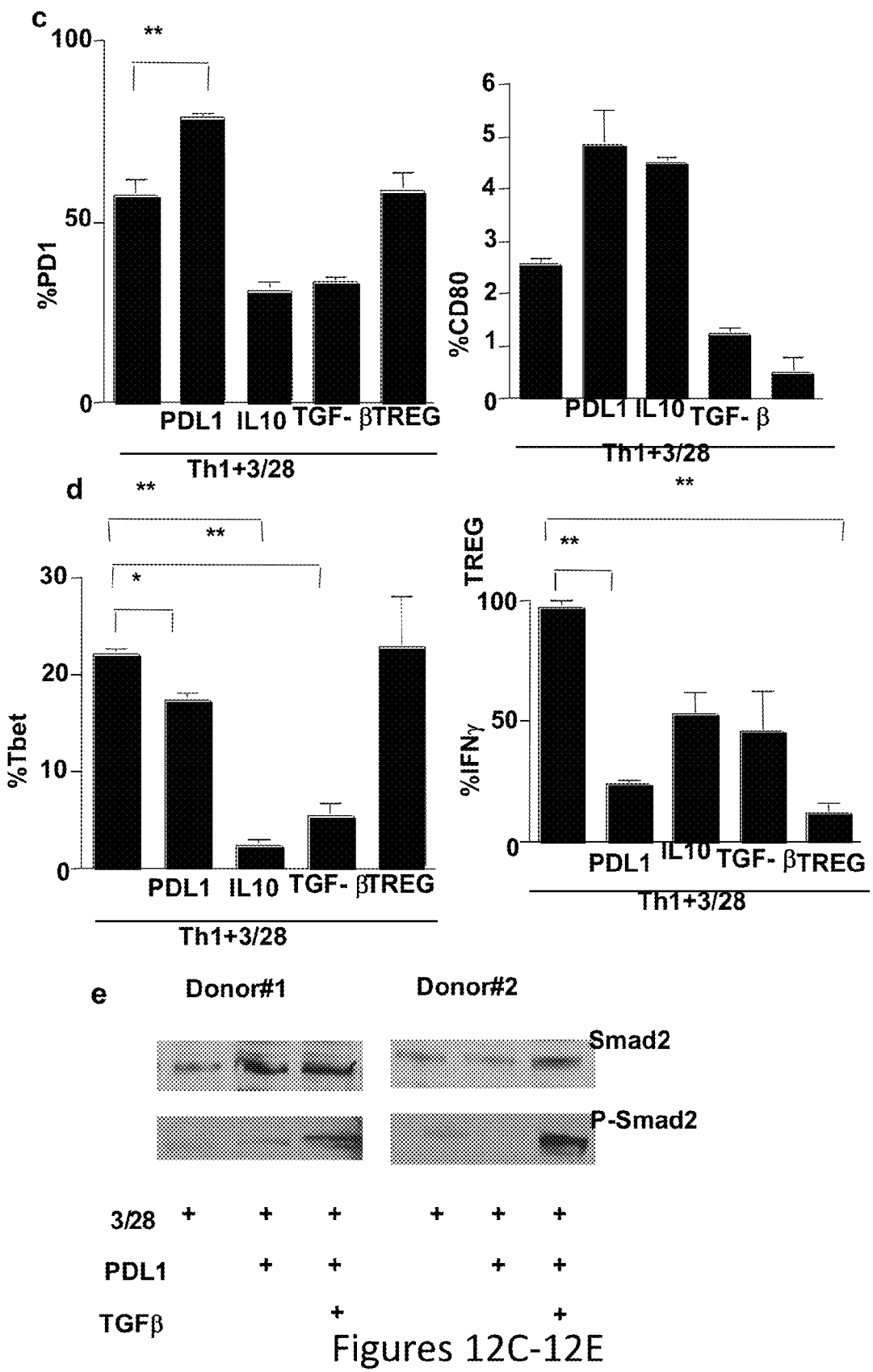

The next experiments were designed to characterize the phenotype of the PDL1-expressing CD4+ and CD8+ T cells, and evaluate whether Th1 cell exposure might modulate the PDL1-expressing T cells (reverse signaling). PDL1 transduction increased T cell expression of BTLA ligands (FIG. 12A, left panels), galectin 9 (FIG. 12A, middle panel), and CD80 (FIG. 12A, right panel) and reduced T cell expression of TBET (FIG. 12B, left panel) and IFN-γ (FIG. 12B, right panel); FOXP3 expression was not altered by PDL1 transduction (FIG. 12B, middle panel). PDL1-transduced T cells that were exposed in vivo to Th1 effectors had decreased expression of BTLA ligands, galectin 9, and CD80 (FIG. 12C) and maintained low expression of TBET and FOXP3 with no significant alteration in IFN-γ production (FIG. 12D). In vitro co-culture of PDL1-expressing T cells with Th1 cells did not significantly alter expression of any of these molecules on the PDL1-expressing T cells (FIGS. 12E; 12F). In sum, these in vivo data may suggest that reverse signaling occurred in the system.

PDL1-Mediated Th1 to $T_{REG}$ Conversion is Durable In Vivo

Figures 3A, 3B, 3C, 3D:
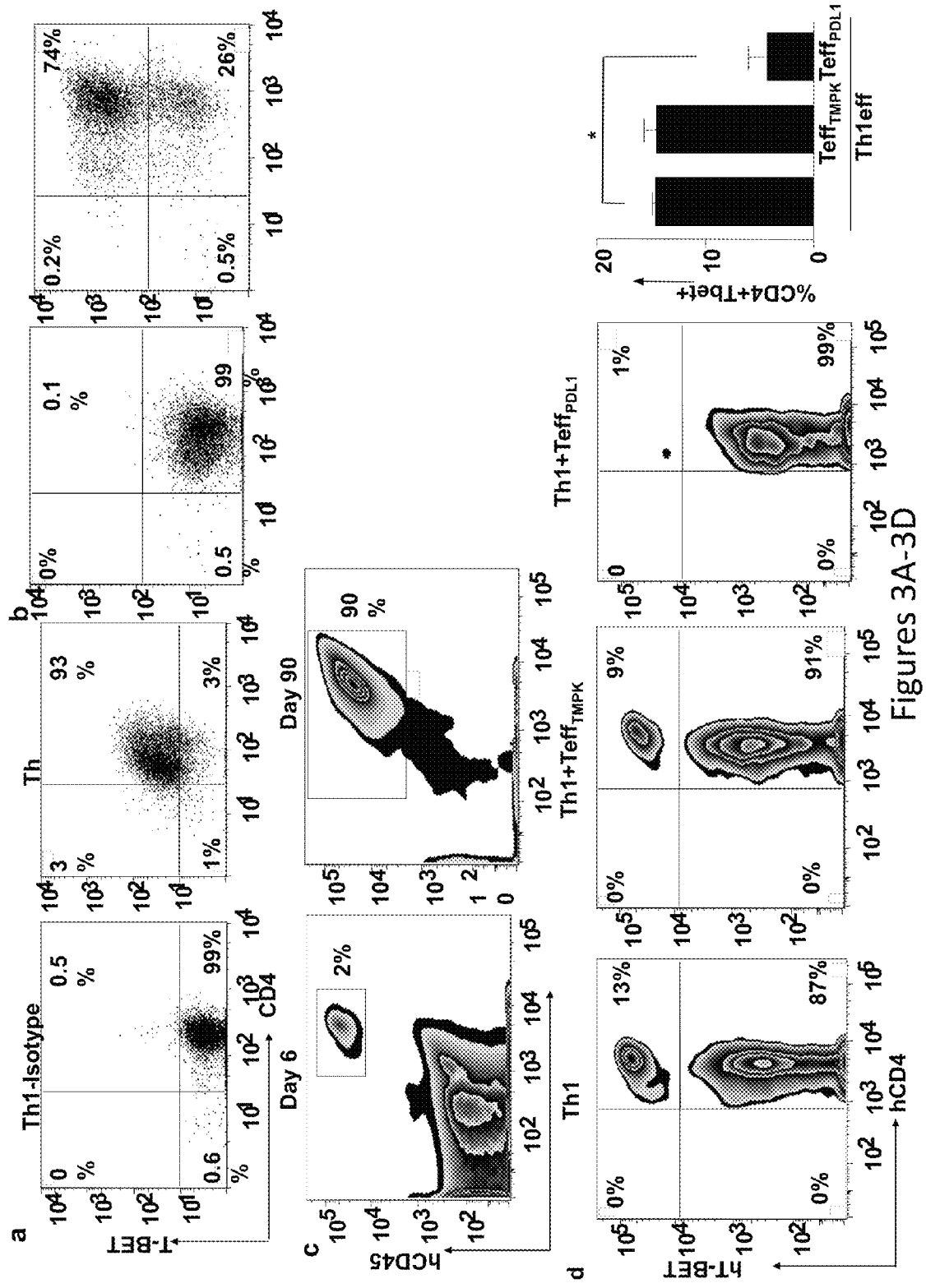
FIGS. 3A through 3G, is a series of images demonstrating that Th1 cells mediate lethal xGVHD and abrogation by PDL1-expressing effector T cells.
Figures 3E, 3F, 3G:
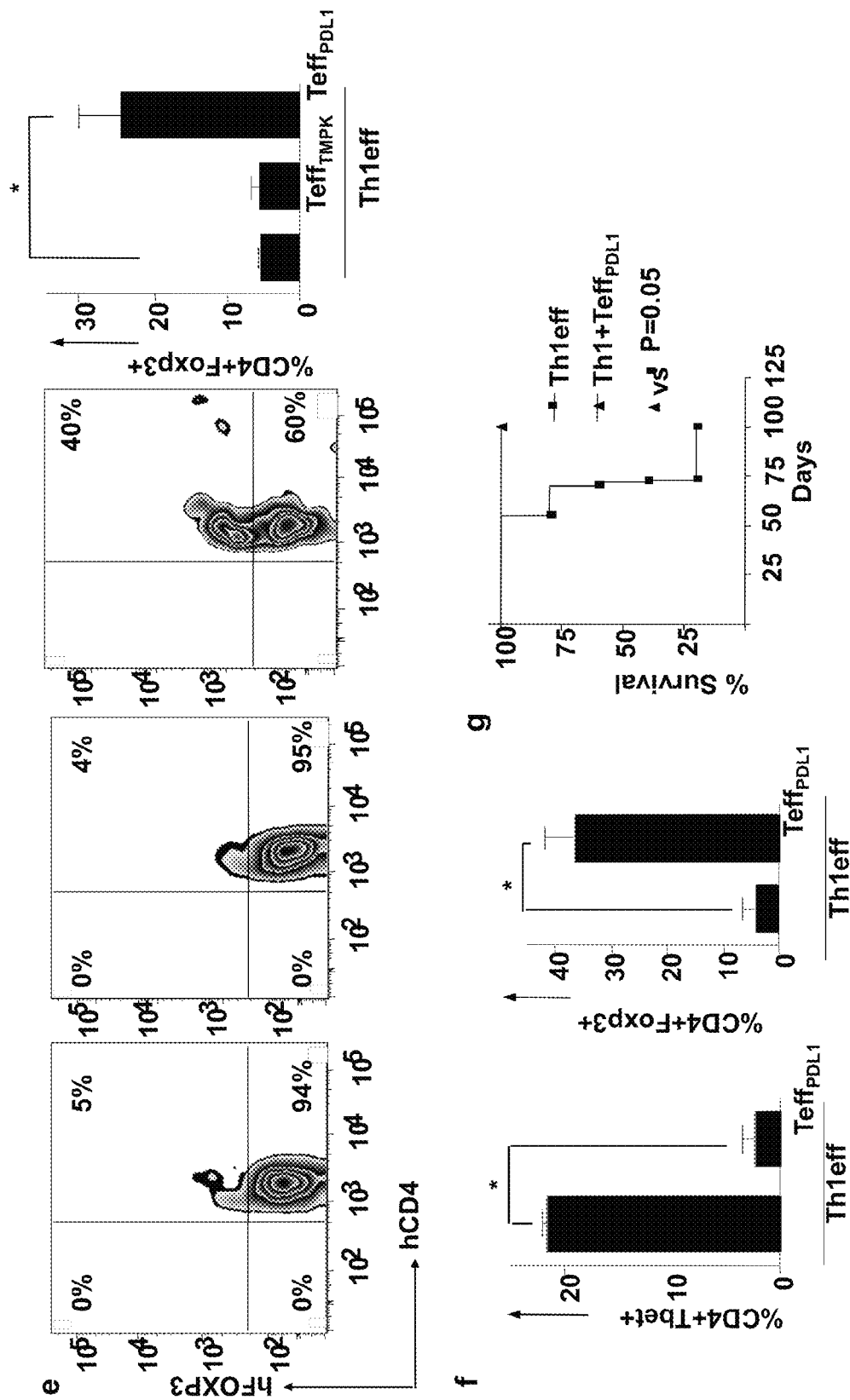

The next experiments were designed to evaluate the long-term stability of the Th1 cell phenotype in vivo during xGVHD. Th1 cells, 93% of which expressed TBET (FIG. 3A), were adoptively transferred into murine recipients either alone or with PDL1-expressing T cells (FIG. 3B). Human Th1 cells engrafted and persisted long-term (FIG. 3C, left and right panel; days 6 and 90 after transplant, respectively). At day 6 after transplant, Th1 cells preferentially expressed TBET (FIG. 3D, left panel) rather than FOXP3 (FIG. 3E, left panel). A similar transcription factor profile was observed in recipients of Th1 cells plus T cells expressing CD19.TMPK alone (FIG. 3D, middle panel; FIG. 3E, middle panel). In contrast, recipients of Th1 cells plus T cells expressing CD19.TMPK/PDL1 had reduced TBET+ T cells (FIG. 3d, right panel) and increased FOXP3+ T cells (FIG. 3E, right panel). This shift in Th1 cell transcription factor expression was observed consistently (FIG. 3D summary plot; FIG. 3E summary plot). At day 90 after transplant, T cells from the minority of Th1 cell recipients that did not undergo lethal xGVHD maintained TBET expression without FOXP3 expression (FIG. 3F). In contrast, recipients of Th1 cells plus PDL1-expressing T cells expressed abundant FOXP3 and dramatically reduced TBET levels (FIG. 3F). Importantly, this conversion of Th1 cells into a regulatory phenotype was associated with complete prevention of xGVHD lethality (FIG. 3G).

Th1 Cell Differentiation Plasticity Requires an Intact PD1 Receptor

Figures 4A, 4B:
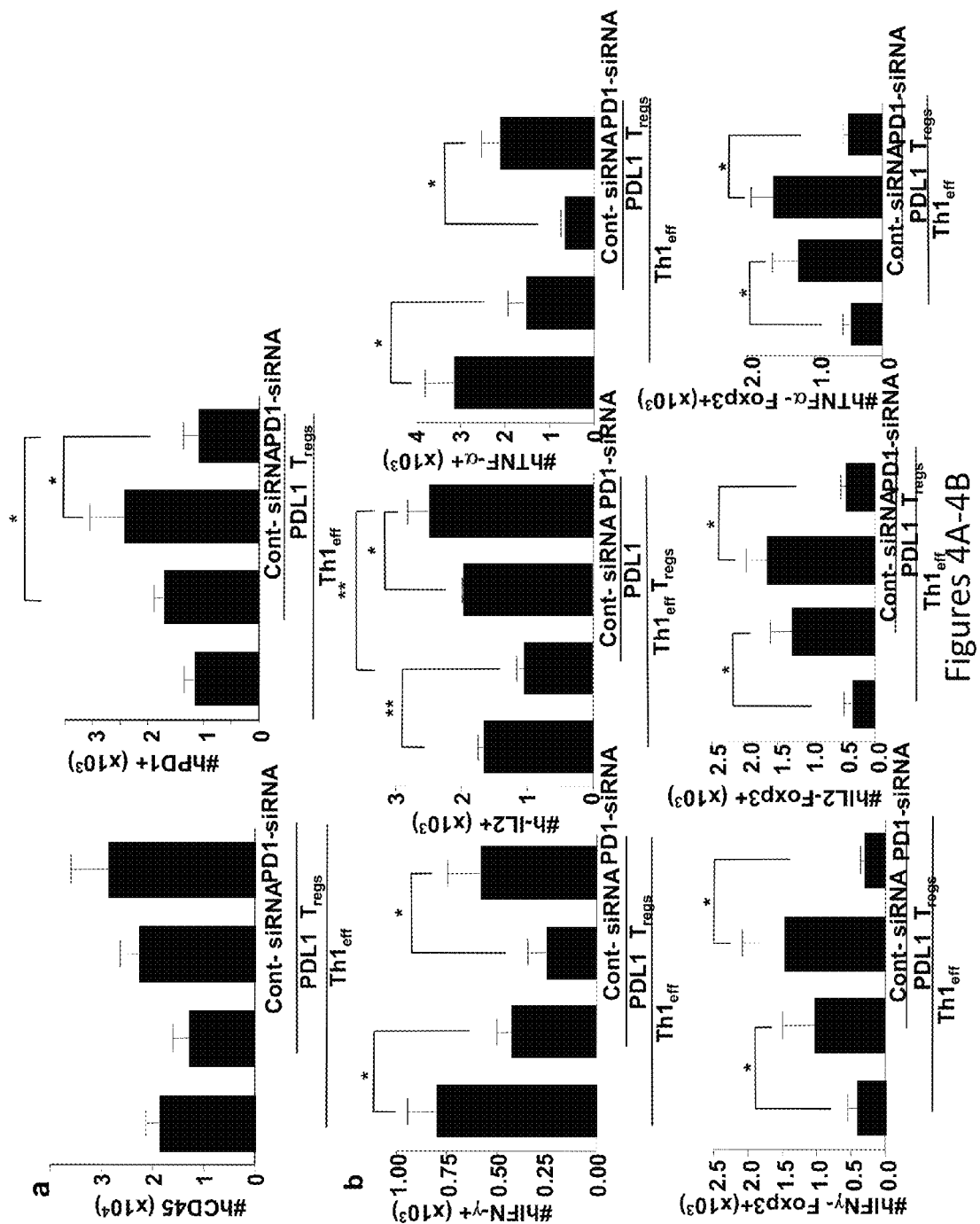
FIGS. 4A through 4E is a series of images demonstrating that PDL1-mediated abrogation of Th1 effector cell function requires intact PD1. NSG host mice received, as indicated, a combination of human Th1 cells (either unmodified, control siRNA-treated, or PD1 siRNA-treated) and PDL1-transduced T cells.
Figures 4C, 4D, 4E:
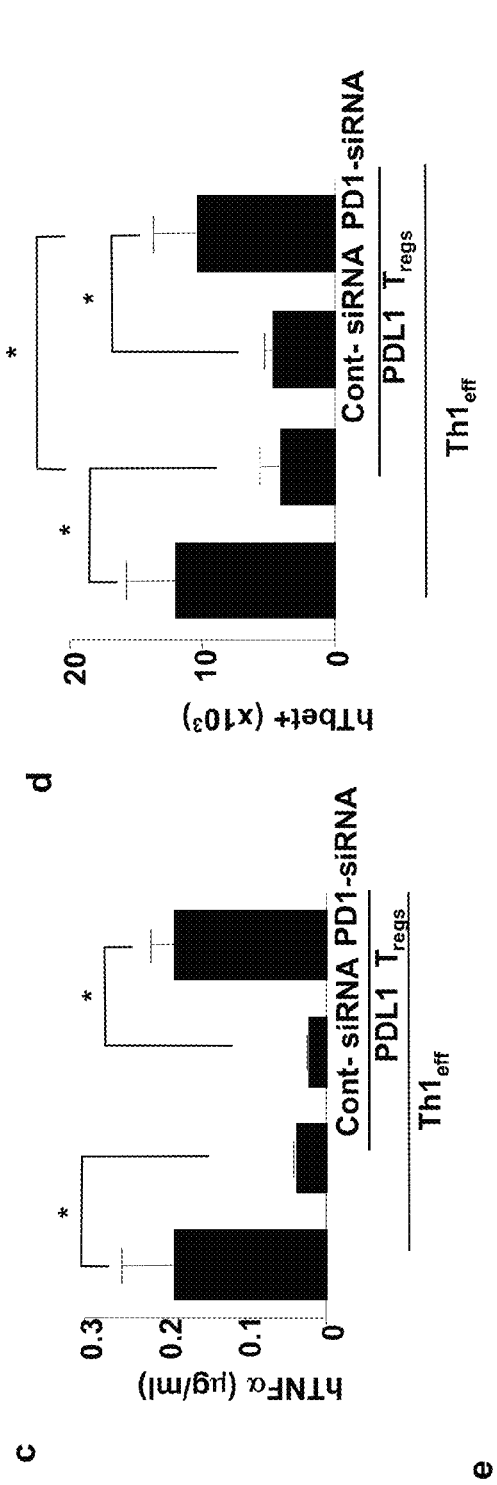

PDL1 can modulate T cell function through binding to PD1 or CD80 (B7.1) (Butte, et al., 2007, Immunity 27:111-122). To determine whether PD1 was operational in the system, in vivo experiments were performed using Th1 cells knocked down for PD1 receptor expression via an siRNA approach (Th1.PD1$^{kd}$). Importantly, Th1.PD1$^{kd}$ cells engrafted similarly to control Th1 cells (FIG. 4A, left panel). Th1 cells had increased PD1 levels in vivo when co-administered with PDL1-expressing T cells; however, engrafted Th1.PD1$^{kd}$ cells did not up-regulate PD1 (FIG. 4A, right panel), thereby confirming in vivo PD1 knock-down. Co-administration of PDL1-expressing T cells reduced Th1 cell-mediated in vivo effector function, as indicated by reduced numbers of FOXP3-negative T cells that were IFN-γ positive, IL-2 positive, and TNF-α-positive (FIG. 4B top panels). In contrast, engrafted Th1.PD1$^{kd}$ cells were relatively resistant to the down-regulatory effect of PDL1-expressing T cells. Furthermore, whereas transfer of PDL1-expressing T cells increased the number of Th1 cells that expressed FOXP3 in the absence of effector cytokine secretion (FIG. 4B; bottom panels), Th1.PD1$^{kd}$ cells did not express this regulatory phenotype in vivo. Following adoptive transfer of PDL1-expressing T cells, Th1.PD1$^{kd}$ cells maintained TBET expression and were fully capable of initiating a systemic TNF-α response that was associated with lethal xGVHD (FIGS. 4C, 4D, and 4E). In sum, these data indicate that PDL1 mediated an in vivo conversion of human Th1 cells towards a $T_{REG}$ phenotype by a mechanism involving the PD1 receptor.

Th1 to $T_{REG}$ Conversion Involves SHP1/SHP2 Signaling

Figures 5A, 5B:
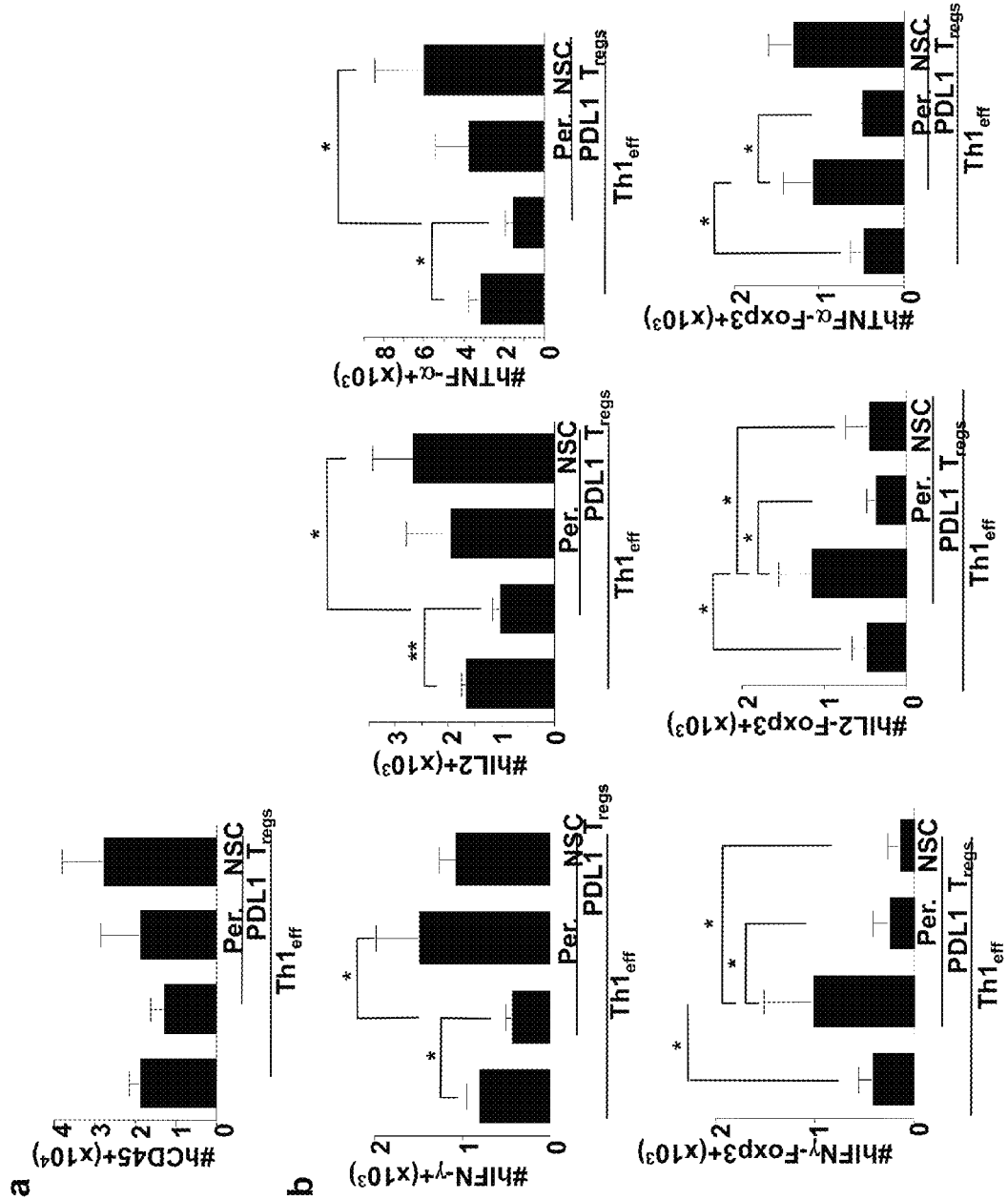
FIGS. 5A through 5E, is a series of images demonstrating that PDL1 induction of Th1 cell plasticity requires intact SHP1/2 signaling. NSG host mice received, as indicated, a combination of human Th1 cells (either unmodified, pervanadate-treated [Per], or NSC87877-treated [NSC]) and PDL1-transduced T cells.
Figures 5C, 5D, 5E:
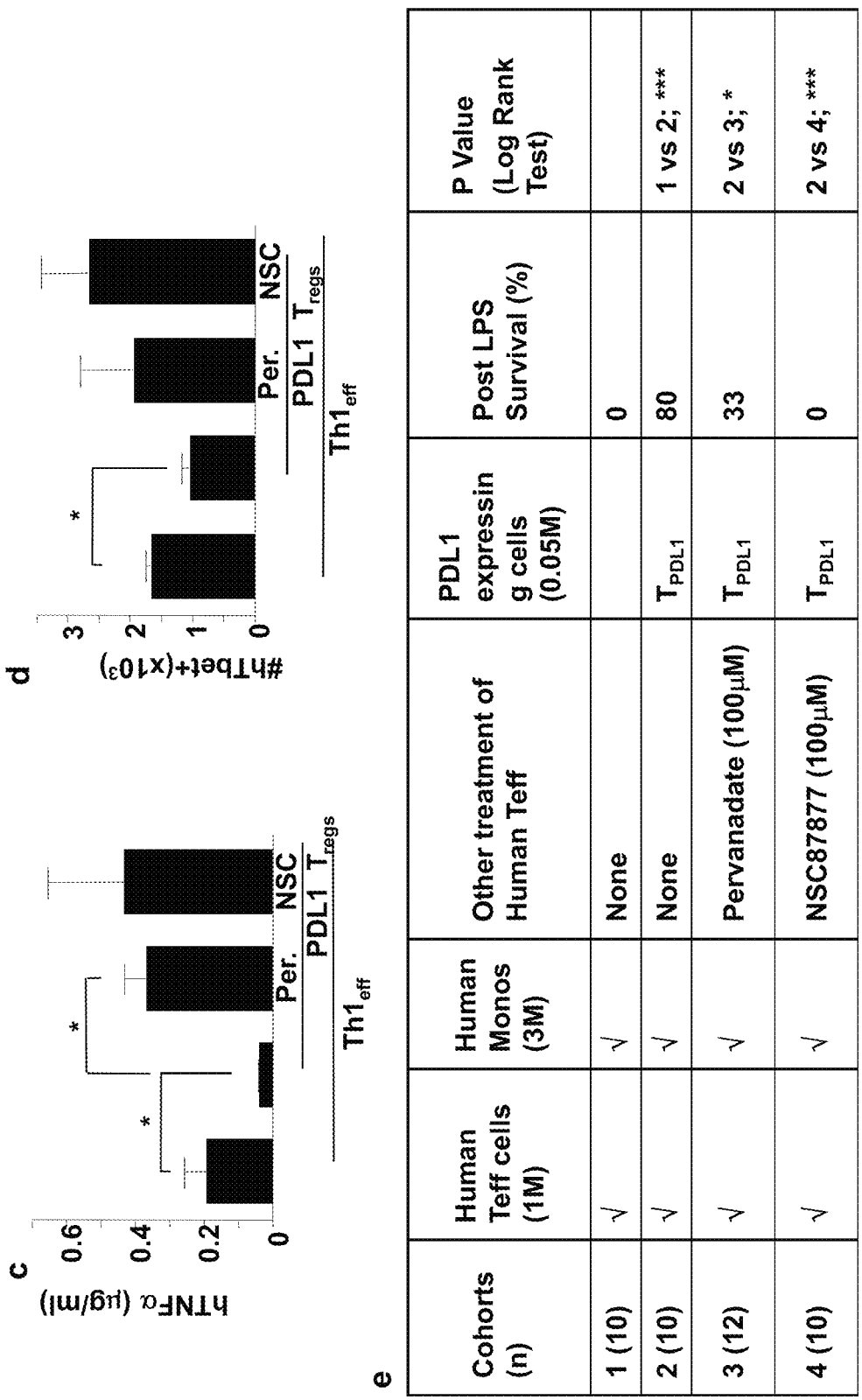

Because PD1 receptor signaling occurs via SHP1/2 (Latchman, et al., 2001, Nat Immunol 2:261-268; Chemnitz, et al., 2004, J Immunol 173:945-954), it is believed that ex vivo pharmacologic inhibition of this pathway using pervanadate (Chemnitz, et al., 2004, J Immunol 173:945-954) or NSC87877 (Chen, et al., 2006, Mol Pharmacol 70:562-570; Song, et al., 2009, Biochem Biophys Res Commun 381: 491-495) might generate Th1 cells (Th1.SHP1/2$^{in}$) resistant to the tolerizing effect of PDL1. SHP1/2 inhibition did not influence Th1 cell engraftment (FIG. 5A). Remarkably, Th1.SHP1/2$^{in}$ cells maintained their effector phenotype in vivo when co-administered with PDL1-expressing T cells, as indicated by preserved or increased expression of IFN-γ, IL-2, and TNF-α (FIG. 5B, top panels) in combination with a reduction of PDL1-mediated up-regulation of FOXP3 (FIG. 5B, bottom panels). Finally, even in the presence of PDL1-expressing T cells, Th1.SHP1/2$^{in}$ cells promoted systemic TNF-α production, had preserved or increased TBET expression, and were potent mediators of lethal xGVHD (FIGS. 5C, 5D, and 5E). Therefore, blockade of PD1 receptor or inhibition of down-stream SHP1/2 signaling prevented PDL1-mediated Th1 cell differentiation plasticity.

PD1 Signaling Reduces Th1 Cell STAT1 Activation

Figure 6A:
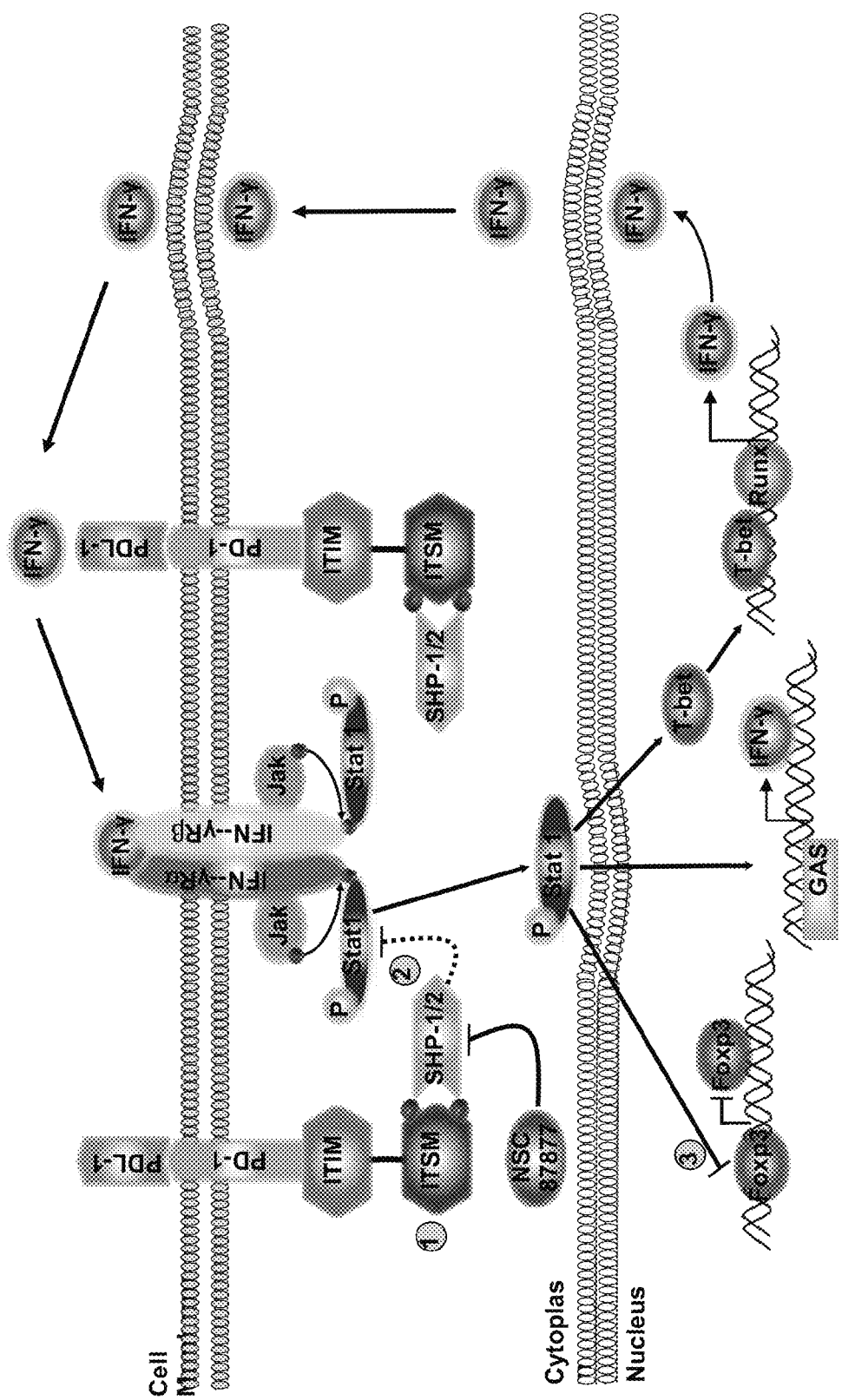
FIGS. 6A through 6E, is a series of images demonstrating that PDL1 induction of Th1 cell plasticity associates with STAT1 inactivation.
Figure 6B:
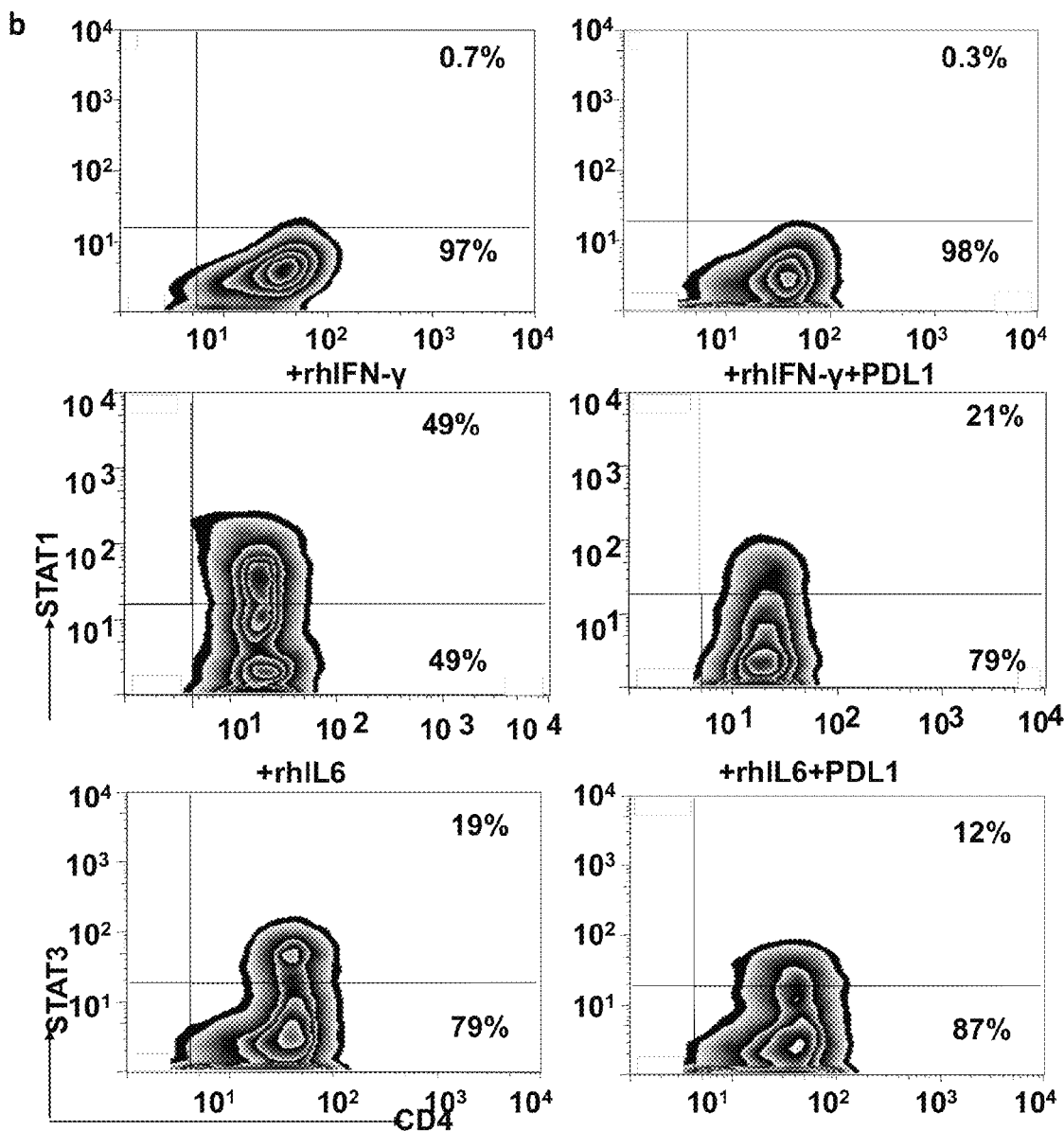
Figures 6C, 6D, 6E:
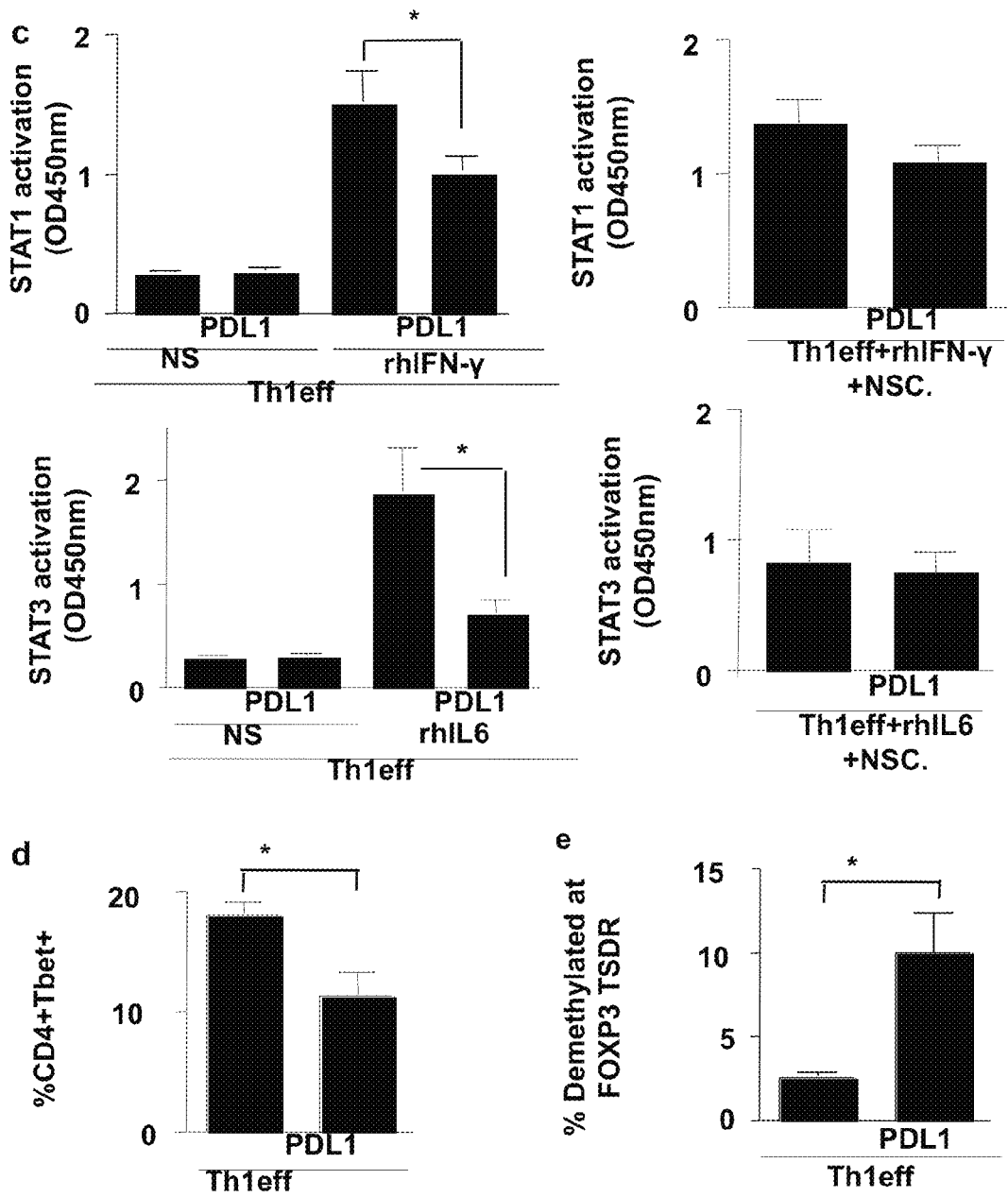
Figures 7A, 7B:
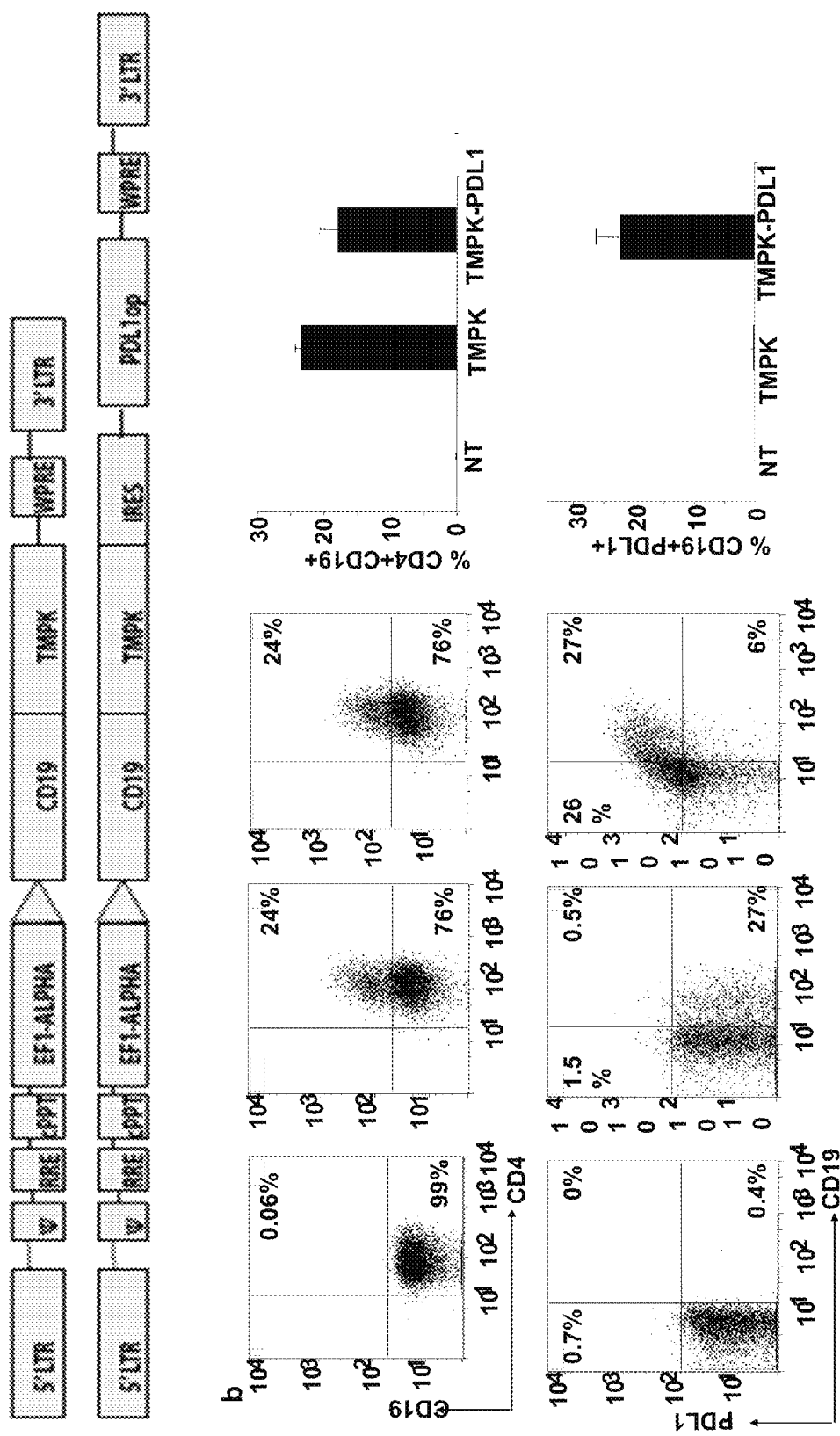
FIGS. 7A through 7E, is a series of images demonstrating that primary human T cells engraft after transduction with lentiviral vector expressing PDL1 and TMPK/CD19 fusion protein.
Figures 7C, 7D, 7E:
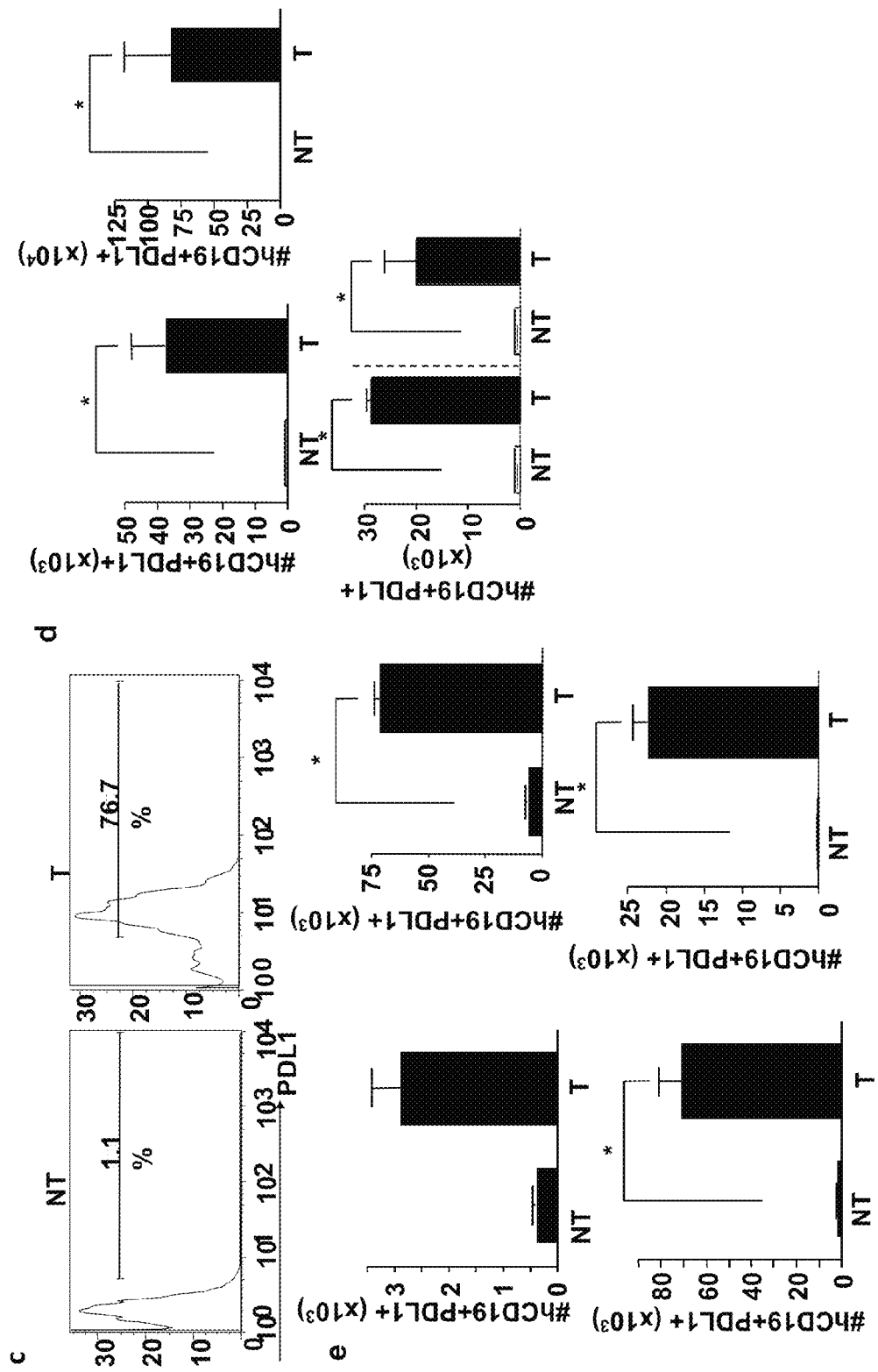
Figures 13A, 13B, 13C, 13D:
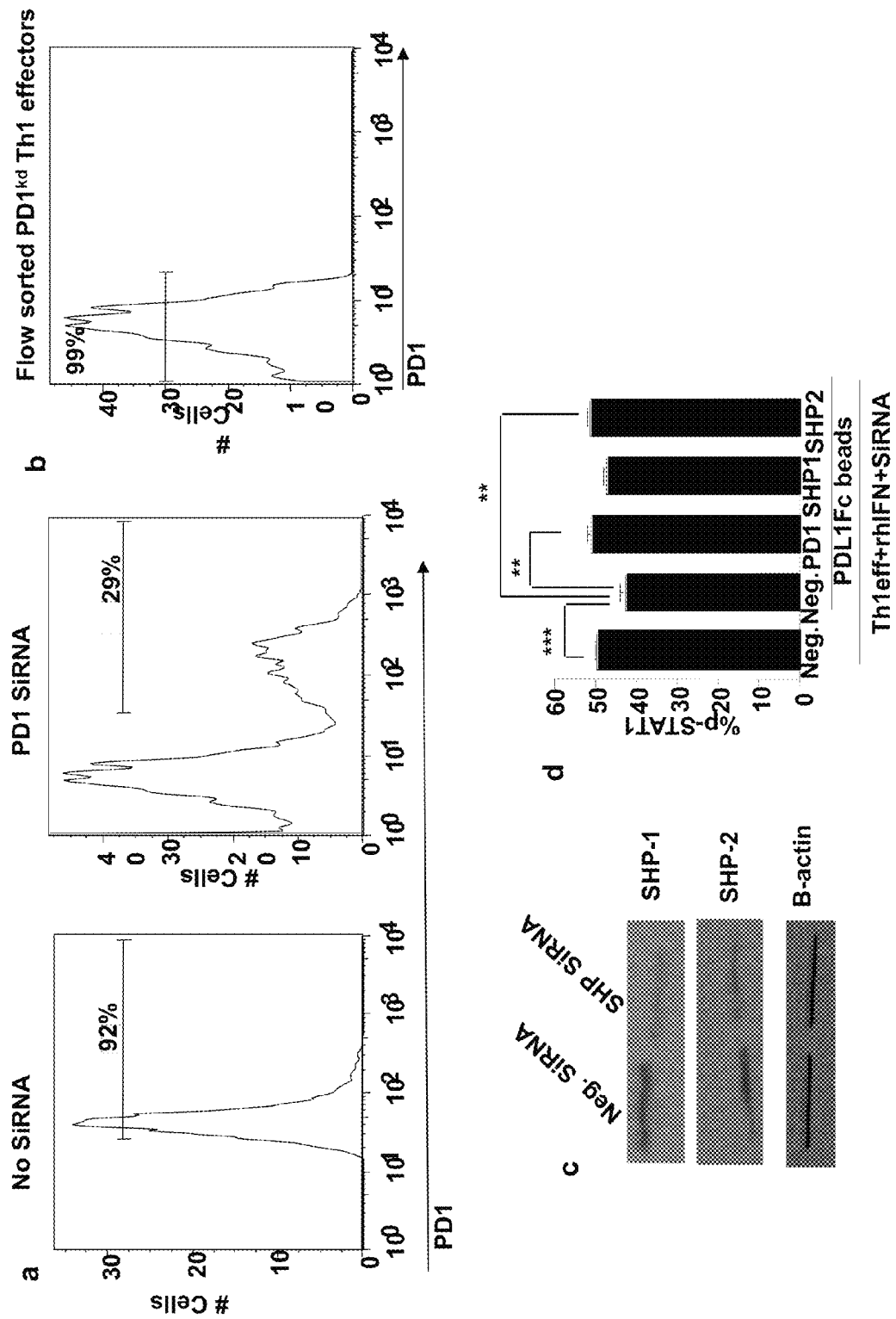
FIGS. 13A through 13D, is a series of imaged demonstrating that PD1 siRNA knocks down PD1 expression and reduces SHP1/2 in human Th1 cells. Human Th1 cells were expanded ex vivo and then were treated with siRNA for PD1.

Using a conditional knockout model, it was previously shown that SHP2 inactivates STAT molecules. Specifically, lack of SHP2 increased STAT3 phosphorylation, thereby resulting in constitutive T cell activation and inflammatory disease (Ohtani, et al., 2000, Immunity 12:95-105). Previous studies have not evaluated whether STAT1, which is critical for maintaining the Th1 phenotype and serves to negatively regulate FOXP3 expression in murine T cells[41], might be similarly down-regulated by SHP1/2 activation. Given this information, experiments were designed to generate a working model (FIG. 6A) whereby SHP1/2 activation might reduce STAT1 phosphorylation, thereby promoting instability of Th1 cell polarity and propagation of FOXP3 expression. Th1 cells were re-stimulated in the presence of the STAT1 activating cytokine IFN-γ either alone or in combination with PDL1-conjugated beads. It was observed that IFN-γ stimulation increased STAT1 phosphorylation (FIG. 6B; FIG. 13A, left panel). In the presence of PDL1, Th1 cells had reduced IFN-γ mediated STAT1 phosphorylation (FIG. 6B, representative data; FIG. 13A left panel). Further experiments were performed to evaluate whether PDL-1 mediated Th1 cell plasticity might be mimicked by other known immunosuppressive molecules. Decreases in Th1 cell STAT1 phosphorylation were observed not only with PDL1 exposure, but also with addition of TGF-β or purified TREG cells (FIG. 13A left panel); Th1 cell co-culture did not modulate STAT1 phosphorylation within the PDL1-transduced T cells. Furthermore, Th1 nuclear STAT1 phosphorylation upon IFN-γ stimulation was also decreased in the presence of PDL1 (FIG. 6C, top left panel). This reduction in nuclear STAT1 phosphorylation was abrogated both by SHP1/2 pharmacologic inhibition (FIG. 6C, top right panel) and siRNA-mediated knock-down of PD1 (FIG. 14D). Th1 cell STAT4 phosphorylation was reduced after PDL1 exposure (FIG. 13B, left panel). Finally, PDL1-transduced T cells were relatively deficient in STAT4 phosphorylation (FIG. 13B, middle panel); after co-culture with Th1 cells, STAT4 phosphorylation in PDL1 expanded cells was not significantly altered by Th1 cell co-culture (FIG. 13B, right panel).

It was observed that the inhibitory effect of SHP1/2 activation on STAT molecules was not limited to STAT1. That is, using IL-6 to activate STAT3, it was observed that PDL1 also inactivated this pathway in Th1 cells (FIG. 6B, representative data). IL-6 driven nuclear STAT3 phosphorylation was also decreased in Th1 cells by PDL1 expression (FIG. 6C, bottom right panel). In this model system, PD1 activation and subsequent reduction in STAT activation was associated with a reduction in Th1 cell expression of TBET and IFN-γ (FIG. 6E; FIG. 13D). Interestingly, Th1 cell exposure to PDL1-coated beads increased the demethylation of the TSDR locus of the FOXP3 gene (FIG. 6F); this effect appeared to occur independently of TGF-β signaling because there was no alteration of p-Smad expression in Th1 cells (FIG. 13E). Addition of IL-10, TGF-β, or purified $T_{REG}$ cells to Th1 cells inhibited STAT1 and STAT4 phosphorylation and reduced TBET and IFN-γ expression in a manner similar to PDL1 exposure (FIGS. 13A, 13B and 13D), did not alter expression of the PDL1 binding partners PD1 or CD80 (FIG. 13C), and did not alter TSDR demethylation (0.2% of Th1 cells demethylated at FOXP3 TSDR). In sum these data indicate that PDL1 mediated Th1 cell plasticity are somewhat unique in relation to other immunological factors.

The PDL1-PD1 Axis Converts Human Th1 Cells into Regulatory T Cells

CD4$^+$ T cells of the Th1 cytokine phenotype, which are essential to cell-mediated immunity against cancer and infectious disease, can be rendered ineffective by multiple down-regulatory mechanisms including antigen-induced cell death (Ramsdell, et al., 1994, Int Immunol 6:1545-1553), anergy due to cytokines such as TGF-β (Li, et al., 1993, Jpn J Cancer Res 84:315-325) or due to surface molecules such as CTLA-4 (Egen, et al., 2002, Nat Immunol 3:611-618) or PDL1 (Chemnitz, et al., 2004, J Immunol 173:945-954; Fife, et al., 2009, Nat Immunol 10:1185-1192), suppression by $T_{REG}$ cells (Lu, et al., 2010, Cell 142:914-929), or conversion to a Th2 phenotype (Sher, et al., 1991, J Immunol 147:2713-2716). The results presented herein demonstrate that human Th1 cells are susceptible to conversion into a $T_{REG}$ phenotype.

The new finding that human Th1 cells can rapidly morph into $T_{REG}$ cells in vivo under the influence of PDL1 provides further evidence that functional T cell subset inter-conversion plays an important role in immune regulation. Because the Th1 cells that we evaluated nearly uniformly expressed TBET and IFN-γ and were relatively devoid of FOXP3 expression, it is unlikely that the rapid, PDL1-induced alteration in Th1 cell phenotype that was observed was due to an outgrowth of "contaminating" $T_{REG}$ cells in the Th1 cell inoculum. Of note, PDL1 modulated both ex vivo generated Th1 cells and human Th1 cells that were demonstrated to be pathogenic on the basis of their induction of xenogeneic GVHD. T-helper cell functional plasticity was initially described in seminal work relating to Th1/Th2 cross-regulation (Sher, et al., 1991, J Immunol 147:2713-2716; Fiorentino, et al., 1989, J Exp Med 170:2081-2095). This Th1/Th2 paradigm has been updated and expanded recently, as it has been demonstrated that Th1 plus Th2 regulation can occur at the single cell level via transcription factor co-expression: Th2 cells under the influence of interferon and IL-12 signaling can gain TBET expression while preserving GATA-3 expression (Hegazy, et al., 2010, Immunity 32:116-128). Another well-described example of CD4$^+$ T cell subset plasticity involves $T_{REG}$ cell susceptibility towards Th17 differentiation via the reprogramming effect of the STAT3 activating cytokines IL-1 and IL-6 (Yang, et al., 2008, Immunity 29:44-56). Importantly, such $T_{REG}$ to Th17 subset in vivo conversion can be alleviated by blocking IL-6, thereby increasing $T_{REG}$ cells and reducing Th1 and Th17 cell-mediated murine GVHD (Chen, et al., 2009, Blood 114:891-900). In still yet another example, non-pathogenic Th17 cells convert in vivo into Th1 cells with subsequent induction of autoimmune diabetes (Martin-Orozco, et al., 2009, Eur J Immunol 39:216-224; Bending, et al., 2009, J Clin Invest 119(3):565-72); IL-12 induced activation of STAT4 in Th17 cells represents an important mechanism for Th17 conversion to IFN-γ secreting, TBET expressing Th1 cells (Lee, et al., 2009, Immunity 30:92-107).

The results presented herein extend the understanding of CD4$^+$ T cell plasticity in two new important directions. First, Th1 cells have never been identified as a subset susceptible to reprogramming to a $T_{REG}$ phenotype; therefore, Th1 cells are both amenable to regulation by $T_{REG}$ cells (Lu, et al., 2010, Cell 142:914-929) and as described here, can indeed become $T_{REG}$ cells under the influence of PDL1. This finding stands somewhat in contrast to observations from a recent study, which found that murine Th1 cells had limited capacity for conversion to a $T_{REG}$ phenotype; indeed, Th1 cells caused a reduction in $T_{REG}$ cell numbers in vivo (Caretto, et al., 2010, J Immunol 184:30-34). Second, previous studies have exclusively focused on differentiation plasticity mediated by cytokine-mediated STAT pathway activation through phosphorylation. Distinct from this prior literature, the results presented herein identified an example of plasticity due to an inhibitory co-stimulatory molecule, PDL1, which reduces Th1 cell STAT activation through the phosphatase function of the SHP1/2 signaling pathway that lies downstream to the PD1 receptor.

In addition to extending an understanding of CD4$^-$ T cell differentiation plasticity, the current results enhance knowledge pertaining to the primacy of PDL1/PD1 interactions in T cell regulation. That is, previous to this report, PD1 suppression of T cell function has been primarily attributed to anergy via SHP1/2 inhibition of TCR activation (Chemnitz, et al., 2004, J Immunol 173:945-954) or to tolerance achieved through blocking of TCR stop signals required for T cell interaction with antigen-expressing dendritic cells (Fife, et al., 2009, Nat Immunol 10:1185-1192). Distinct from these prior reports, it was found that PDL1/PD1 interactions caused the in vivo conversion of effector Th1 cells into $T_{REG}$ cells; in the present model, this form of T cell differentiation plasticity was tolerizing, as evidenced by the inability of an otherwise lethal inocula of Th1 cells to mediate xenogeneic GVHD. As such, PD1-mediated T cell tolerance can be attained by inhibition of T cell activation, or as shown herein, by altering T cell differentiation. Based on these findings, it is now possible to propose that the increased frequency of $T_{REG}$ cells in the tumor microenvironment may relate not only to an indirect mechanism of $T_{REG}$ recruitment by CCL22 elaborated in response to inflammation from infiltrating anti-tumor Th1 cells (Gobert et al., 2009, Cancer Res 69:2000-2009) but also from a direct mechanism of tumor cell PDL1-mediated conversion of Th1 cells to a $T_{REG}$ phenotype.

The current findings also point to new clinical translational approaches. First, it was found that pre-treatment of adoptively-transferred Th1 cells with anti-PD1 siRNA or SHP1/2 pharmacologic inhibitors successfully abrogated PDL1-mediated conversion to a $T_{REG}$ phenotype and fully restored Th1 cell capacity to mediate lethal xGVHD. Of note, anti-PD1 monoclonal antibodies are being evaluated in early-stage clinical trials and have shown promising anti-tumor effects (reviewed in (Kline and Gajewski, 2010, Curr Opin Investig Drugs 11:1354-1359)); given the results presented herein, it will be desirable to determine whether recipients of anti-PD1 therapies have preservation of a Th1 cytokine phenotype. And, it is possible that adoptive transfer of Th1 cells in combination with an anti-PD1 strategy might represent an approach to preserve the in vivo phenotype of Th1 cell therapy. Alternatively, the data presented herein indicate that it may be possible to use SHP1/2 inhibitors, which are currently being evaluated in pre-clinical models (Kline and Gajewski, 2010, Curr Opin Investig Drugs 11:1354-1359), for the protection of adoptively transferred Th1 cells against $T_{REG}$ cell conversion. It is important to note that the present experiments utilized either T cells or immortalized K562 tumor cells to deliver the tolererizing PDL1 signal and that it will thus be essential to determine whether a similar biology occurs in the tumor microenvironment.

Second, it was found that PDL1-mediated erosion of an otherwise stable Th1 phenotype was associated with lower levels of STAT activation, thereby implying that PDL1/PD1 interactions may operate in part by reducing a tonic level of STAT activation required for protection of the Th1 state. In clinical trials of adoptive T cell therapy, IL-2 is the cytokine most commonly administered in combination with T cell infusion (Robbins, et al., 2011, J Clin Oncol 29:917-924). The present data suggest that IFN-α or IL-12, which activate the Th1-dedicated pathways STAT1 and STAT4, respectively, might also be evaluated in combination with adoptive T cell therapy to preserve the Th1 state in vivo; of note, in animal models, T cells engineered to secrete IL-12 represent particularly potent anti-tumor effectors (Kerkar, et al., 2010, Cancer Res 70:6725-6734).

It was also found that T cells genetically engineered to express PDL1 prevented lethal xenogeneic GVHD in a similar manner as purified $T_{REG}$ cells. These data suggest that the treatment of GVHD, prevention of solid organ graft rejection, or modulation of autoimmunity might be harnessed through a PDL1 gene transfer approach as an alternative to ongoing $T_{REG}$ cell therapy strategies (Riley, et al., 2009, Immunity 30:656-665). PDL1-modulation of Th1 cells inhibited xGVHD in two distinct in vivo models. Of note, multiple cellular vehicles for the PDL1 gene transfer (namely, CD4+ and CD8+ T cells and K562 myeloid tumor cells) were capable of modulating Th1 cells, thereby indicating the flexibility of such a PDL1-mediated therapy.

Th1 cells, which are critical for anti-tumor and anti-infection immunity, are subjected to numerous previously described counter-regulatory mechanisms, and as described here, appear to also face the challenge of PDL1-mediated conversion to a $T_{REG}$ phenotype. Without wishing to be bound by any particular theory, it is believed that adoptive T cell therapy clinical trials can be performed to evaluate whether Th1 cell function can be preserved in vivo through anti-PD1 reagents, SHP1/2 inhibitors, or modulation of specific STAT pathways. In addition, it is believed that cellular vehicles engineered for PDL1 expression might be evaluated as a surrogate for regulatory T cell therapy of autoimmunity or GVHD.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of converting a pathogenic T cell into a cell that exhibits a regulatory T cell phenotype, the method comprising contacting the pathogenic T cell with a K562 cell modified to express an agent selected from the group consisting of PDL1, PDL2, and an anti-PD1 antibody, thereby converting said pathogenic T cell into a cell that exhibits a regulatory T cell phenotype.

2. The method of claim 1, wherein said pathogenic T cell is a non-regulatory T cell selected from the group consisting of a CD4$^+$ cell, a CD4$^+$CD25$^-$ cell, and a CD4$^+$CD25$^-$45RA$^+$ cell.

3. The method of claim 1, wherein said pathogenic T cell is selected from the group consisting of a Th1 cell, a Th2 cell, a Th17 cell, and any combination thereof.

4. The method of claim 1, wherein said converted regulatory T cell exhibits a phenotype selected from the group consisting of expression of Foxp3, suppression of effector T cell activation, and a combination thereof.

5. The method of claim 1, wherein said modified K562 cell is irradiated.

6. The method of claim 1, wherein said pathogenic T cell induces graft vs host disease (GVHD).

* * * * *